(12) United States Patent
Cahill

(10) Patent No.: US 9,949,728 B2
(45) Date of Patent: *Apr. 24, 2018

(54) SEPTAL CLOSURE DEVICE WITH CENTERING MECHANISM

(71) Applicant: W. L. Gore & Associates, Inc., Newark, DE (US)

(72) Inventor: Ryan Cahill, Newark, DE (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/642,238

(22) Filed: Mar. 9, 2015

(65) Prior Publication Data

US 2015/0182209 A1  Jul. 2, 2015

Related U.S. Application Data

(63) Continuation of application No. 12/062,904, filed on Apr. 4, 2008, now Pat. No. 9,005,242.

(Continued)

(51) Int. Cl.
*A61B 17/08* (2006.01)
*A61B 17/00* (2006.01)

(52) U.S. Cl.
CPC *A61B 17/0057* (2013.01); *A61B 2017/00575* (2013.01); *A61B 2017/00592* (2013.01);
(Continued)

(58) Field of Classification Search
CPC ...... A61B 2017/00247; A61B 17/0057; A61B 17/00575; A61B 2017/00606
See application file for complete search history.

(56) References Cited

U.S. PATENT DOCUMENTS 283,653 A    8/1883   Paxson
3,294,631 A  12/1966  Lorenz et al.
(Continued)

FOREIGN PATENT DOCUMENTS

CN    1218379 A    6/1999
CN    1247460 A    3/2000
(Continued)

OTHER PUBLICATIONS

Chinese Search Report in Application No. 200980158768.9, dated Jun. 16, 2013, 4 pages.

(Continued)

*Primary Examiner* — Gregory Anderson
*Assistant Examiner* — Christina Lauer

(57) ABSTRACT

In one aspect, the present invention provides a device for occluding an aperture in a body, for example, a patent foramen ovale (PFO), including a first side adapted to be disposed on one side of the septum and a second side adapted to be disposed on the opposite side of the septum. The device has an elongated, low-profile delivery configuration and a shortened, radially expanded deployment configuration. The first and second sides are adapted to occlude the aperture upon deployment of the device at its intended delivery location. The device also includes a radially expandable center portion. In some embodiments, the center portion includes a plurality of ribs provided by slits in device. The ribs expand radially when the device is deployed. The expandable center portion facilitates the positioning of the device in the aperture. The device can be secured in the deployed configuration using a catch system.

17 Claims, 8 Drawing Sheets

Related U.S. Application Data

(60) Provisional application No. 60/921,969, filed on Apr. 5, 2007.

(52) U.S. Cl.
CPC .............. A61B 2017/00597 (2013.01); A61B 2017/00606 (2013.01); A61B 2017/00619 (2013.01); A61B 2017/00623 (2013.01); A61B 2017/00654 (2013.01); A61B 2017/00676 (2013.01)

(56) References Cited

U.S. PATENT DOCUMENTS

| | | |
|---|---|---|
| 3,324,518 A | 6/1967 | Louderback |
| 3,447,533 A | 6/1969 | Spicer |
| 3,739,770 A | 6/1973 | Mori |
| 3,784,388 A | 1/1974 | King et al. |
| 3,824,631 A | 7/1974 | Burstein et al. |
| 3,874,388 A | 4/1975 | King et al. |
| 3,875,648 A | 4/1975 | Bone |
| 3,907,675 A | 9/1975 | Chapurlat et al. |
| 3,924,631 A | 12/1975 | Mancusi, Jr. |
| 3,939,849 A | 2/1976 | Baxter et al. |
| 4,006,747 A | 2/1977 | Kronenthal et al. |
| 4,007,743 A | 2/1977 | Blake |
| 4,038,365 A | 7/1977 | Patil et al. |
| 4,113,912 A | 9/1978 | Okita |
| 4,149,327 A | 4/1979 | Hammer et al. |
| 4,193,138 A | 3/1980 | Okita |
| 4,425,908 A | 1/1984 | Simon |
| 4,525,374 A | 6/1985 | Vaillancourt |
| 4,610,674 A | 9/1986 | Suzuki et al. |
| 4,619,246 A | 10/1986 | Molgaard et al. |
| 4,626,245 A | 12/1986 | Weinstein |
| 4,693,249 A | 9/1987 | Schenck et al. |
| 4,696,300 A | 9/1987 | Anderson |
| 4,710,181 A | 12/1987 | Fuqua |
| 4,710,192 A | 12/1987 | Liotta et al. |
| 4,738,666 A | 4/1988 | Fuqua |
| 4,766,898 A | 8/1988 | Hardy et al. |
| 4,796,612 A | 1/1989 | Reese |
| 4,832,055 A | 5/1989 | Palestrant |
| 4,836,204 A | 6/1989 | Landymore et al. |
| 4,840,623 A | 6/1989 | Quackenbush |
| 4,902,508 A | 2/1990 | Badylak et al. |
| 4,915,107 A | 4/1990 | Rebuffat et al. |
| 4,917,089 A | 4/1990 | Sideris |
| 4,917,793 A | 4/1990 | Pitt et al. |
| 4,921,479 A | 5/1990 | Grayzel |
| 4,956,178 A | 9/1990 | Badylak et al. |
| 5,021,059 A | 6/1991 | Kensey et al. |
| 5,037,433 A | 8/1991 | Wilk et al. |
| 5,041,129 A | 8/1991 | Hayhurst et al. |
| 5,041,225 A | 8/1991 | Norman |
| 5,049,131 A | 9/1991 | Deuss |
| 5,049,275 A | 9/1991 | Gillberg-LaForce et al. |
| 5,078,736 A | 1/1992 | Behl |
| 5,090,422 A | 2/1992 | Dahl et al. |
| 5,098,440 A | 3/1992 | Hillstead |
| 5,106,913 A | 4/1992 | Yamaguchi et al. |
| 5,108,420 A | 4/1992 | Marks |
| 5,124,109 A | 6/1992 | Drossbach |
| 5,149,327 A | 9/1992 | Oshiyama |
| 5,152,144 A | 10/1992 | Andrie |
| 5,163,131 A | 11/1992 | Row et al. |
| 5,167,363 A | 12/1992 | Adkinson et al. |
| 5,167,637 A | 12/1992 | Okada et al. |
| 5,171,259 A | 12/1992 | Inoue |
| 5,176,659 A | 1/1993 | Mancini |
| 5,192,301 A | 3/1993 | Kamiya et al. |
| 5,222,974 A | 6/1993 | Kensey et al. |
| 5,226,879 A | 7/1993 | Ensminger et al. |
| 5,234,458 A | 8/1993 | Metais |
| 5,236,440 A | 8/1993 | Hlavacek |
| 5,245,023 A | 9/1993 | Peoples et al. |
| 5,245,080 A | 9/1993 | Aubard et al. |
| 5,250,430 A | 10/1993 | Peoples et al. |
| 5,257,637 A | 11/1993 | El Gazayerli |
| 5,269,809 A | 12/1993 | Hayhurst et al. |
| 5,275,826 A | 1/1994 | Badylak et al. |
| 5,282,827 A | 2/1994 | Kensey et al. |
| 5,284,488 A | 2/1994 | Sideris |
| 5,304,184 A | 4/1994 | Hathaway et al. |
| 5,312,341 A | 5/1994 | Turi |
| 5,312,435 A | 5/1994 | Nash et al. |
| 5,316,262 A | 5/1994 | Koebler |
| 5,320,611 A | 6/1994 | Bonutti et al. |
| 5,334,217 A | 8/1994 | Das |
| 5,342,393 A | 8/1994 | Stack |
| 5,350,363 A | 9/1994 | Goode et al. |
| 5,350,399 A | 9/1994 | Erlebacher et al. |
| 5,354,308 A | 10/1994 | Simon et al. |
| 5,364,356 A | 11/1994 | Hofling |
| 5,397,331 A | 3/1995 | Himpens et al. |
| 5,411,481 A | 5/1995 | Allen et al. |
| 5,413,584 A | 5/1995 | Schulze |
| 5,417,699 A | 5/1995 | Klein et al. |
| 5,425,744 A | 6/1995 | Fagan et al. |
| 5,433,727 A | 7/1995 | Sideris |
| 5,437,288 A | 8/1995 | Schwartz et al. |
| 5,443,972 A | 8/1995 | Kohama et al. |
| 5,451,235 A | 9/1995 | Lock et al. |
| 5,453,099 A | 9/1995 | Lee et al. |
| 5,478,353 A | 12/1995 | Yoon |
| 5,480,353 A | 1/1996 | Garza, Jr. |
| 5,480,424 A | 1/1996 | Cox |
| 5,486,193 A | 1/1996 | Bourne et al. |
| 5,507,811 A | 4/1996 | Koike et al. |
| 5,571,169 A | 5/1996 | Plaia et al. |
| 5,534,432 A | 7/1996 | Peoples et al. |
| 5,540,712 A | 7/1996 | Kleshinski et al. |
| 5,549,959 A | 8/1996 | Compton |
| 5,562,632 A | 10/1996 | Davila et al. |
| 5,562,728 A | 10/1996 | Lazarus et al. |
| 5,575,816 A | 11/1996 | Rudnick et al. |
| 5,577,299 A | 11/1996 | Thompson et al. |
| 5,578,045 A | 11/1996 | Das |
| 5,591,206 A | 1/1997 | Moufarrege |
| 5,601,571 A | 2/1997 | Moss |
| 5,603,703 A | 2/1997 | Elsberry et al. |
| 5,618,311 A | 4/1997 | Gryskiewicz |
| 5,620,461 A | 4/1997 | Muijs Van De Moer et al. |
| 5,626,599 A | 5/1997 | Bourne et al. |
| 5,634,936 A | 6/1997 | Linden et al. |
| 5,649,950 A | 7/1997 | Bourne et al. |
| 5,649,959 A | 7/1997 | Hannam et al. |
| 5,662,701 A | 9/1997 | Plaia et al. |
| 5,663,063 A | 9/1997 | Peoples et al. |
| 5,683,411 A | 11/1997 | Kavteladze et al. |
| 5,690,674 A | 11/1997 | Diaz |
| 5,693,085 A | 12/1997 | Buirge et al. |
| 5,702,421 A | 12/1997 | Schneidt |
| 5,709,707 A | 1/1998 | Lock et al. |
| 5,713,864 A | 2/1998 | Verkaart |
| 5,713,948 A | 2/1998 | Ulfacker |
| 5,717,259 A | 2/1998 | Schexnayder |
| 5,720,754 A | 2/1998 | Middleman et al. |
| 5,725,552 A | 3/1998 | Kotula et al. |
| 5,725,553 A | 3/1998 | Moenning |
| 5,733,294 A | 3/1998 | Forber et al. |
| 5,733,337 A | 3/1998 | Carr, Jr. et al. |
| 5,741,297 A | 4/1998 | Simon |
| 5,749,880 A | 5/1998 | Banas et al. |
| 5,755,762 A | 5/1998 | Bush |
| 5,769,882 A | 6/1998 | Fogarty et al. |
| 5,772,641 A | 6/1998 | Wilson |
| 5,776,162 A | 7/1998 | Kleshinski |
| 5,776,183 A | 7/1998 | Kanesaka et al. |
| 5,782,847 A | 7/1998 | Plaia et al. |
| 5,782,860 A | 7/1998 | Epstein et al. |
| 5,797,960 A | 8/1998 | Stevens et al. |
| 5,799,384 A | 9/1998 | Schwartz et al. |
| 5,800,436 A | 9/1998 | Lerch |

(56) References Cited

U.S. PATENT DOCUMENTS

| | | |
|---|---|---|
| 5,800,516 A | 9/1998 | Fine et al. |
| 5,810,884 A | 9/1998 | Kim |
| 5,820,594 A | 10/1998 | Fontirroche et al. |
| 5,823,956 A | 10/1998 | Roth et al. |
| 5,829,447 A | 11/1998 | Stevens et al. |
| 5,835,422 A | 11/1998 | Merritt |
| 5,853,420 A | 12/1998 | Chevillon et al. |
| 5,853,422 A | 12/1998 | Huebsch et al. |
| 5,855,614 A | 1/1999 | Stevens et al. |
| 5,861,003 A | 1/1999 | Latson et al. |
| 5,865,791 A | 2/1999 | Whayne et al. |
| 5,865,844 A | 2/1999 | Plaia et al. |
| 5,873,905 A | 2/1999 | Plaia et al. |
| 5,879,366 A | 3/1999 | Shaw et al. |
| 5,893,856 A | 4/1999 | Jacob et al. |
| 5,895,411 A | 4/1999 | Irie |
| 5,897,955 A | 4/1999 | Drumheller |
| 5,902,287 A | 5/1999 | Martin |
| 5,902,319 A | 5/1999 | Daley |
| 5,902,745 A | 5/1999 | Butler et al. |
| 5,904,703 A | 5/1999 | Gilson |
| 5,906,639 A | 5/1999 | Rudnick et al. |
| 5,919,200 A | 7/1999 | Stambaugh et al. |
| 5,924,424 A | 7/1999 | Stevens et al. |
| 5,925,060 A | 7/1999 | Forber |
| 5,928,250 A | 7/1999 | Koike et al. |
| 5,944,691 A | 8/1999 | Querns et al. |
| 5,944,738 A | 8/1999 | Amplatz et al. |
| 5,955,110 A | 9/1999 | Patel et al. |
| 5,957,490 A | 9/1999 | Sinnhuber |
| 5,957,953 A | 9/1999 | DiPoto et al. |
| 5,967,490 A | 10/1999 | Pike |
| 5,976,174 A | 11/1999 | Ruiz |
| 5,980,505 A | 11/1999 | Wilson |
| 5,989,268 A | 11/1999 | Pugsley, Jr. et al. |
| 5,993,475 A | 11/1999 | Lin et al. |
| 5,993,844 A | 11/1999 | Abraham et al. |
| 5,997,575 A | 12/1999 | Whitson et al. |
| 6,010,517 A | 1/2000 | Baccaro |
| 6,016,846 A | 1/2000 | Knittel et al. |
| 6,019,753 A | 2/2000 | Pagan |
| 6,024,756 A | 2/2000 | Huebsch et al. |
| 6,027,519 A | 2/2000 | Stanford |
| 6,030,007 A | 2/2000 | Bassily et al. |
| 6,051,007 A | 4/2000 | Hogendijk et al. |
| 6,053,939 A | 4/2000 | Okuda et al. |
| 6,056,760 A | 5/2000 | Koike et al. |
| 6,071,998 A | 6/2000 | Muller et al. |
| 6,074,401 A | 6/2000 | Gardiner et al. |
| 6,077,281 A | 6/2000 | Das |
| 6,077,291 A | 6/2000 | Das |
| 6,077,880 A | 6/2000 | Castillo et al. |
| 6,079,414 A | 6/2000 | Roth |
| 6,080,182 A | 6/2000 | Shaw et al. |
| 6,080,183 A | 6/2000 | Tsugita et al. |
| 6,096,347 A | 8/2000 | Geddes et al. |
| 6,106,913 A | 8/2000 | Scardino et al. |
| 6,113,609 A | 9/2000 | Adams |
| 6,117,159 A | 9/2000 | Huebsch et al. |
| 6,123,715 A | 9/2000 | Amplatz |
| 6,126,686 A | 10/2000 | Badylak et al. |
| 6,132,438 A | 10/2000 | Fleischman et al. |
| 6,143,037 A | 11/2000 | Goldstein et al. |
| 6,152,144 A | 11/2000 | Lesh et al. |
| 6,165,183 A | 12/2000 | Kuehn et al. |
| 6,165,204 A | 12/2000 | Levinson et al. |
| 6,168,588 B1 | 1/2001 | Wilson |
| 6,171,329 B1 | 1/2001 | Shaw et al. |
| 6,174,322 B1 | 1/2001 | Schneidt et al. |
| 6,174,330 B1 | 1/2001 | Stinson |
| 6,183,443 B1 | 2/2001 | Kratoska et al. |
| 6,183,496 B1 | 2/2001 | Urbanski |
| 6,187,039 B1 | 2/2001 | Hiles et al. |
| 6,190,353 B1 | 2/2001 | Makower et al. |
| 6,190,357 B1 | 2/2001 | Ferrari et al. |
| 6,197,016 B1 | 3/2001 | Fourkas et al. |
| 6,199,262 B1 | 3/2001 | Martin |
| 6,206,895 B1 | 3/2001 | Levinson |
| 6,206,907 B1 | 3/2001 | Marino et al. |
| 6,214,029 B1 | 4/2001 | Thill et al. |
| 6,217,590 B1 | 4/2001 | Levinson |
| 6,221,092 B1 | 4/2001 | Koike et al. |
| 6,227,139 B1 | 5/2001 | Nguyen et al. |
| 6,228,097 B1 | 5/2001 | Levinson et al. |
| 6,231,561 B1 | 5/2001 | Frazier et al. |
| 6,245,080 B1 | 6/2001 | Levinson |
| 6,245,537 B1 | 6/2001 | Williams et al. |
| 6,258,091 B1 | 7/2001 | Sevrain et al. |
| 6,261,309 B1 | 7/2001 | Urbanski |
| 6,265,333 B1 | 7/2001 | Dzenis et al. |
| 6,270,500 B1 | 8/2001 | Lerch |
| 6,270,515 B1 | 8/2001 | Linden et al. |
| 6,277,138 B1 | 8/2001 | Levinson et al. |
| 6,277,139 B1 | 8/2001 | Levinson et al. |
| 6,287,317 B1 | 9/2001 | Makower et al. |
| 6,290,674 B1 | 9/2001 | Roue et al. |
| 6,290,689 B1 | 9/2001 | Delaney et al. |
| 6,290,721 B1 | 9/2001 | Heath |
| 6,299,635 B1 | 10/2001 | Frantzen |
| 6,306,150 B1 | 10/2001 | Levinson |
| 6,306,424 B1 | 10/2001 | Vyakarnam et al. |
| 6,312,443 B1 | 11/2001 | Stone |
| 6,312,446 B1 | 11/2001 | Huebsch et al. |
| 6,315,791 B1 | 11/2001 | Gingras et al. |
| 6,316,262 B1 | 11/2001 | Huisman et al. |
| 6,319,263 B1 | 11/2001 | Levinson |
| 6,322,548 B1 | 11/2001 | Payne et al. |
| 6,328,427 B1 | 12/2001 | Frazier et al. |
| 6,328,727 B1 | 12/2001 | Frazier et al. |
| 6,334,872 B1 | 1/2002 | Termin et al. |
| 6,342,064 B1 | 1/2002 | Koike et al. |
| 6,344,048 B1 | 2/2002 | Chin et al. |
| 6,344,049 B1 | 2/2002 | Levinson et al. |
| 6,346,074 B1 | 2/2002 | Roth |
| 6,348,041 B1 | 2/2002 | Klint |
| 6,352,552 B1 | 3/2002 | Levinson et al. |
| 6,355,052 B1 | 3/2002 | Neuss et al. |
| 6,356,782 B1 | 3/2002 | Sirimanne et al. |
| 6,358,238 B1 | 3/2002 | Sherry |
| 6,364,853 B1 | 4/2002 | French et al. |
| 6,368,338 B1 | 4/2002 | Konya et al. |
| 6,371,904 B1 | 4/2002 | Sirimanne et al. |
| 6,375,625 B1 | 4/2002 | French et al. |
| 6,375,668 B1 | 4/2002 | Gifford et al. |
| 6,375,671 B1 | 4/2002 | Kobayashi et al. |
| 6,379,342 B1 | 4/2002 | Levinson |
| 6,379,363 B1 | 4/2002 | Herrington et al. |
| 6,379,368 B1 | 4/2002 | Corcoran et al. |
| 6,387,104 B1 | 5/2002 | Pugsley, Jr. et al. |
| 6,398,796 B2 | 6/2002 | Levinson |
| 6,402,772 B1 | 6/2002 | Amplatz et al. |
| 6,419,669 B1 | 7/2002 | Frazier et al. |
| 6,426,145 B1 | 7/2002 | Moroni |
| 6,436,088 B2 | 8/2002 | Frazier et al. |
| 6,440,152 B1 | 8/2002 | Gainor et al. |
| 6,443,972 B1 | 9/2002 | Bosma et al. |
| 6,450,987 B1 | 9/2002 | Kramer |
| 6,460,749 B1 | 10/2002 | Levinson et al. |
| 6,468,303 B1 | 10/2002 | Amplatz et al. |
| 6,478,773 B1 | 11/2002 | Gandhi et al. |
| 6,482,224 B1 | 11/2002 | Michler et al. |
| 6,488,706 B1 | 12/2002 | Solymar et al. |
| 6,491,714 B1 | 12/2002 | Bennett |
| 6,494,846 B1 | 12/2002 | Margolis |
| 6,494,888 B1 | 12/2002 | Laufer et al. |
| 6,497,709 B1 | 12/2002 | Heath |
| 6,506,204 B2 | 1/2003 | Mazzocchi |
| 6,508,828 B1 | 1/2003 | Akerfeldt et al. |
| 6,514,515 B1 | 2/2003 | Williams |
| 6,548,569 B1 | 4/2003 | Williams et al. |
| 6,551,303 B1 | 4/2003 | Van Tassel et al. |
| 6,551,344 B2 | 4/2003 | Thill |
| 6,554,849 B1 | 4/2003 | Jones et al. |
| 6,585,719 B2 | 7/2003 | Wang |

(56) References Cited

U.S. PATENT DOCUMENTS

| | | |
|---|---|---|
| 6,585,755 B2 | 7/2003 | Jackson et al. |
| 6,589,251 B2 | 7/2003 | Yee et al. |
| 6,596,013 B2 | 7/2003 | Yang et al. |
| 6,599,448 B1 | 7/2003 | Ehrhard, Jr. et al. |
| 6,610,764 B1 | 8/2003 | Martin et al. |
| 6,623,506 B2 | 9/2003 | McGuckin et al. |
| 6,623,508 B2 | 9/2003 | Shaw et al. |
| 6,623,518 B2 | 9/2003 | Thompson et al. |
| 6,626,936 B2 | 9/2003 | Stinson |
| 6,629,901 B2 | 10/2003 | Huang |
| 6,652,556 B1 | 11/2003 | VanTassel et al. |
| 6,666,861 B1 | 12/2003 | Grabek |
| 6,669,707 B1 | 12/2003 | Swanstrom et al. |
| 6,669,713 B2 | 12/2003 | Adams |
| 6,669,722 B2 | 12/2003 | Chen et al. |
| 6,685,707 B2 | 2/2004 | Roman et al. |
| 6,689,589 B2 | 2/2004 | Huisman et al. |
| 6,712,804 B2 | 3/2004 | Roue et al. |
| 6,712,836 B1 | 3/2004 | Berg et al. |
| 6,726,696 B1 | 4/2004 | Houser et al. |
| 6,755,834 B2 | 6/2004 | Amis |
| 6,786,915 B2 | 9/2004 | Akerfeldt et al. |
| 6,828,357 B1 | 12/2004 | Martin et al. |
| 6,838,493 B2 | 1/2005 | Williams et al. |
| 6,855,126 B2 | 2/2005 | Flinchbaugh |
| 6,860,895 B1 | 3/2005 | Akerfeldt et al. |
| 6,866,669 B2 | 3/2005 | Buzzard et al. |
| 6,867,247 B2 | 3/2005 | Williams et al. |
| 6,867,248 B1 | 3/2005 | Martin et al. |
| 6,867,249 B2 | 3/2005 | Lee |
| 6,921,401 B2 | 7/2005 | Lerch et al. |
| 6,921,410 B2 | 7/2005 | Porter |
| 6,939,352 B2 | 9/2005 | Buzzard et al. |
| 6,994,092 B2 | 2/2006 | Van Der Burg et al. |
| 7,044,134 B2 | 5/2006 | Khairkhahan et al. |
| 7,048,738 B1 | 5/2006 | Wellisz et al. |
| 7,097,653 B2 | 8/2006 | Freudenthal et al. |
| 7,128,073 B1 | 10/2006 | van der Burg et al. |
| 7,149,587 B2 | 12/2006 | Wardle et al. |
| 7,152,605 B2 | 12/2006 | Khairkhahan et al. |
| 7,165,552 B2 | 1/2007 | Deem et al. |
| 7,198,631 B2 | 4/2007 | Kanner et al. |
| 7,207,402 B2 | 4/2007 | Bjoerk |
| 7,223,271 B2 | 5/2007 | Muramatsu et al. |
| 7,238,188 B2 | 7/2007 | Nesper et al. |
| 7,335,426 B2 | 2/2008 | Marton et al. |
| 7,361,178 B2 | 4/2008 | Hearn et al. |
| 7,381,216 B2 | 6/2008 | Buzzard et al. |
| 7,431,729 B2 | 10/2008 | Chanduszko |
| 7,452,363 B2 | 11/2008 | Ortiz |
| 7,481,832 B1 | 1/2009 | Meridew et al. |
| 7,582,104 B2 | 9/2009 | Corcoan et al. |
| 7,597,704 B2 | 10/2009 | Frazier et al. |
| 7,658,748 B2 | 2/2010 | Marino et al. |
| 7,678,123 B2 | 3/2010 | Chanduszko |
| 7,704,268 B2 | 4/2010 | Chanduszko et al. |
| 7,735,493 B2 | 6/2010 | van der Burg et al. |
| 7,780,700 B2 | 8/2010 | Frazier et al. |
| 7,842,053 B2 | 11/2010 | Chanduszko et al. |
| 7,871,419 B2 | 1/2011 | Devellian et al. |
| 7,875,052 B2 | 1/2011 | Kawaura et al. |
| 7,887,562 B2 | 2/2011 | Young et al. |
| 7,905,901 B2 | 3/2011 | Corocan et al. |
| 7,918,872 B2 | 4/2011 | Mitelberg et al. |
| 8,034,061 B2 | 10/2011 | Amplatz et al. |
| 8,062,325 B2 | 11/2011 | Mitelberg et al. |
| 8,118,833 B2 | 2/2012 | Seibold et al. |
| 8,257,389 B2 | 9/2012 | Chanduszko et al. |
| 8,277,480 B2 | 10/2012 | Callaghan et al. |
| 8,308,760 B2 | 11/2012 | Chanduszko |
| 8,361,110 B2 | 1/2013 | Chanduszko |
| 8,480,706 B2 | 7/2013 | Chanduszko et al. |
| 8,551,135 B2 | 10/2013 | Kladakis et al. |
| 8,753,362 B2 | 6/2014 | Widomski et al. |
| 8,764,790 B2 * | 7/2014 | Thommen .......... A61B 17/0057 606/213 |
| 8,764,848 B2 | 7/2014 | Callaghan |
| 8,821,528 B2 | 9/2014 | McGuckin et al. |
| 8,858,576 B2 | 10/2014 | Takahashi et al. |
| 9,005,242 B2 | 4/2015 | Cahill |
| 9,119,607 B2 | 9/2015 | Amin |
| 9,138,213 B2 | 9/2015 | Amin et al. |
| 9,326,759 B2 | 5/2016 | Chanduszko et al. |
| 9,474,517 B2 | 10/2016 | Amin et al. |
| 2001/0010481 A1 | 8/2001 | Blanc et al. |
| 2001/0014800 A1 | 8/2001 | Frazier et al. |
| 2001/0025132 A1 | 9/2001 | Alferness et al. |
| 2001/0034537 A1 | 10/2001 | Shaw et al. |
| 2001/0034567 A1 | 10/2001 | Allen et al. |
| 2001/0037129 A1 | 11/2001 | Thill |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0044639 A1 | 11/2001 | Levinson |
| 2001/0049492 A1 | 12/2001 | Frazier et al. |
| 2001/0049551 A1 | 12/2001 | Tseng et al. |
| 2002/0010481 A1 | 1/2002 | Jayaraman |
| 2002/0019648 A1 | 2/2002 | Akerfeldt et al. |
| 2002/0022859 A1 | 2/2002 | Hogendijk |
| 2002/0022860 A1 | 2/2002 | Borillo et al. |
| 2002/0026208 A1 | 2/2002 | Roe et al. |
| 2002/0029048 A1 | 3/2002 | Miller |
| 2002/0032459 A1 | 3/2002 | Horzewski et al. |
| 2002/0032462 A1 | 3/2002 | Houser et al. |
| 2002/0034259 A1 | 3/2002 | Tada |
| 2002/0035374 A1 | 3/2002 | Borillo et al. |
| 2002/0043307 A1 | 4/2002 | Ishida et al. |
| 2002/0049457 A1 | 4/2002 | Kaplan et al. |
| 2002/0052572 A1 | 5/2002 | Franco et al. |
| 2002/0058980 A1 | 5/2002 | Sass |
| 2002/0058989 A1 | 5/2002 | Chen et al. |
| 2002/0077555 A1 | 6/2002 | Schwartz |
| 2002/0095174 A1 | 7/2002 | Tsugita et al. |
| 2002/0095183 A1 | 7/2002 | Casset et al. |
| 2002/0096183 A1 | 7/2002 | Stevens et al. |
| 2002/0099389 A1 | 7/2002 | Michler et al. |
| 2002/0099390 A1 | 7/2002 | Kaplan et al. |
| 2002/0099437 A1 | 7/2002 | Anson et al. |
| 2002/0103492 A1 | 8/2002 | Kaplan et al. |
| 2002/0107531 A1 | 8/2002 | Schreck et al. |
| 2002/0111537 A1 | 8/2002 | Taylor et al. |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0143292 A1 | 10/2002 | Flinchbaugh |
| 2002/0156475 A1 | 10/2002 | Lerch et al. |
| 2002/0156499 A1 | 10/2002 | Konya et al. |
| 2002/0164729 A1 | 11/2002 | Skraly et al. |
| 2002/0169377 A1 | 11/2002 | Khairkhahan et al. |
| 2002/0183786 A1 | 12/2002 | Girton |
| 2002/0183787 A1 | 12/2002 | Wahr et al. |
| 2002/0183823 A1 | 12/2002 | Pappu |
| 2002/0198563 A1 | 12/2002 | Gainor et al. |
| 2003/0004533 A1 | 1/2003 | Dieck et al. |
| 2003/0023266 A1 | 1/2003 | Welch et al. |
| 2003/0028213 A1 | 2/2003 | Thill et al. |
| 2003/0045893 A1 | 3/2003 | Ginn |
| 2003/0050665 A1 | 3/2003 | Ginn |
| 2003/0055455 A1 | 3/2003 | Yang et al. |
| 2003/0057156 A1 | 3/2003 | Peterson et al. |
| 2003/0059640 A1 | 3/2003 | Marton et al. |
| 2003/0065379 A1 | 4/2003 | Babbs et al. |
| 2003/0100920 A1 | 5/2003 | Akin et al. |
| 2003/0113868 A1 | 6/2003 | Flor et al. |
| 2003/0120337 A1 | 6/2003 | Van Tassel et al. |
| 2003/0130683 A1 | 7/2003 | Andreas et al. |
| 2003/0139819 A1 | 7/2003 | Beer et al. |
| 2003/0150821 A1 | 8/2003 | Bates et al. |
| 2003/0171774 A1 | 9/2003 | Seigner et al. |
| 2003/0187390 A1 | 10/2003 | Bates et al. |

(56) References Cited

U.S. PATENT DOCUMENTS

| | | |
|---|---|---|
| 2003/0191495 A1 | 10/2003 | Ryan et al. |
| 2003/0195530 A1 | 10/2003 | Thill |
| 2003/0195555 A1 | 10/2003 | Khairkhahan et al. |
| 2003/0204203 A1 | 10/2003 | Khairkhahan et al. |
| 2003/0225421 A1 | 12/2003 | Peavey et al. |
| 2003/0225439 A1 | 12/2003 | Cook et al. |
| 2004/0006330 A1 | 1/2004 | Fangrow |
| 2004/0044361 A1 | 3/2004 | Frazier et al. |
| 2004/0044364 A1 | 3/2004 | DeVries et al. |
| 2004/0073242 A1 | 4/2004 | Chanduszko |
| 2004/0098042 A1 | 5/2004 | Devellian |
| 2004/0116959 A1 | 6/2004 | McGuckin et al. |
| 2004/0127919 A1 | 7/2004 | Trout et al. |
| 2004/0133230 A1 | 7/2004 | Carpenter et al. |
| 2004/0133236 A1 | 7/2004 | Chanduszko |
| 2004/0143294 A1 | 7/2004 | Corcoran et al. |
| 2004/0167566 A1 | 8/2004 | Beulke et al. |
| 2004/0176799 A1 | 9/2004 | Chanduszko et al. |
| 2004/0186510 A1 | 9/2004 | Weaver |
| 2004/0210301 A1 | 10/2004 | Obermiller |
| 2004/0220596 A1 | 11/2004 | Frazier et al. |
| 2004/0220610 A1 | 11/2004 | Kreidler et al. |
| 2004/0230222 A1 | 11/2004 | van der Burg et al. |
| 2004/0234567 A1 | 11/2004 | Dawson |
| 2004/0254594 A1 | 12/2004 | Alfaro |
| 2005/0025809 A1 | 2/2005 | Hasirci et al. |
| 2005/0038470 A1 | 2/2005 | Van Der Burg et al. |
| 2005/0043759 A1* | 2/2005 | Chanduszko ...... A61B 17/0057 606/213 |
| 2005/0055039 A1 | 3/2005 | Burnett et al. |
| 2005/0065548 A1 | 3/2005 | Marino et al. |
| 2005/0067523 A1 | 3/2005 | Zach et al. |
| 2005/0070935 A1 | 3/2005 | Ortiz |
| 2005/0080476 A1 | 4/2005 | Gunderson et al. |
| 2005/0113868 A1 | 5/2005 | Devellian |
| 2005/0119690 A1 | 6/2005 | Mazzocchi et al. |
| 2005/0182426 A1 | 8/2005 | Adams et al. |
| 2005/0187564 A1 | 8/2005 | Jayaraman |
| 2005/0187568 A1 | 8/2005 | Klenk et al. |
| 2005/0192626 A1 | 9/2005 | Widomski et al. |
| 2005/0192627 A1 | 9/2005 | Whisenant et al. |
| 2005/0267523 A1 | 12/2005 | Devellian et al. |
| 2005/0267525 A1* | 12/2005 | Chanduszko ...... A61B 17/0057 606/213 |
| 2005/0267572 A1 | 12/2005 | Schoon et al. |
| 2005/0273135 A1 | 12/2005 | Chanduszko et al. |
| 2005/0288706 A1 | 12/2005 | Widomski et al. |
| 2005/0288786 A1 | 12/2005 | Chanduszko |
| 2006/0020332 A1 | 1/2006 | Lashinski et al. |
| 2006/0025790 A1 | 2/2006 | de Winter et al. |
| 2006/0030884 A1 | 2/2006 | Yeung et al. |
| 2006/0106447 A1 | 5/2006 | Opolski |
| 2006/0109073 A1 | 5/2006 | Allison et al. |
| 2006/0116710 A1 | 6/2006 | Corcoran et al. |
| 2006/0122646 A1 | 6/2006 | Corcoran et al. |
| 2006/0122647 A1 | 6/2006 | Callaghan et al. |
| 2006/0167494 A1 | 7/2006 | Suddaby |
| 2006/0206148 A1 | 9/2006 | Khairkhahan et al. |
| 2006/0217764 A1 | 9/2006 | Abbott et al. |
| 2006/0224183 A1 | 10/2006 | Freudenthal |
| 2006/0235463 A1 | 10/2006 | Freudenthal et al. |
| 2006/0241690 A1 | 10/2006 | Amplatz et al. |
| 2006/0265004 A1 | 11/2006 | Callaghan et al. |
| 2006/0271089 A1 | 11/2006 | Alejandro et al. |
| 2006/0276839 A1 | 12/2006 | McGuckin |
| 2007/0010851 A1 | 1/2007 | Chanduszko et al. |
| 2007/0066994 A1 | 3/2007 | Blaeser et al. |
| 2007/0112381 A1 | 5/2007 | Figulla et al. |
| 2007/0118176 A1 | 5/2007 | Opolski et al. |
| 2007/0129755 A1 | 6/2007 | Abbott et al. |
| 2007/0167981 A1 | 7/2007 | Opolski |
| 2007/0179474 A1 | 8/2007 | Cahill et al. |
| 2007/0185529 A1 | 8/2007 | Coleman et al. |
| 2007/0191884 A1 | 8/2007 | Eskridge et al. |
| 2007/0225760 A1 | 9/2007 | Moszner et al. |
| 2007/0244517 A1 | 10/2007 | Callaghan et al. |
| 2007/0244518 A1 | 10/2007 | Callaghan |
| 2007/0250081 A1 | 10/2007 | Cahill et al. |
| 2007/0250115 A1 | 10/2007 | Opolski et al. |
| 2007/0265656 A1 | 11/2007 | Amplatz |
| 2007/0276415 A1 | 11/2007 | Kladakis et al. |
| 2007/0282430 A1 | 12/2007 | Thommen et al. |
| 2008/0015633 A1 | 1/2008 | Abbott et al. |
| 2008/0058800 A1 | 3/2008 | Collins et al. |
| 2008/0065149 A1 | 3/2008 | Thielen et al. |
| 2008/0077180 A1 | 3/2008 | Kladakis et al. |
| 2008/0086168 A1 | 4/2008 | Cahill et al. |
| 2008/0091234 A1 | 4/2008 | Kladakis et al. |
| 2008/0109073 A1 | 5/2008 | Lashinski et al. |
| 2008/0119886 A1 | 5/2008 | Greenhalgh et al. |
| 2008/0119891 A1 | 5/2008 | Miles et al. |
| 2008/0147111 A1 | 6/2008 | Johnson et al. |
| 2008/0208214 A1 | 8/2008 | Sato et al. |
| 2008/0228218 A1 | 9/2008 | Chanduszko |
| 2008/0249562 A1 | 10/2008 | Cahill et al. |
| 2008/0262518 A1 | 10/2008 | Freudenthal |
| 2009/0012559 A1 | 1/2009 | Chanduszko |
| 2009/0054912 A1 | 3/2009 | Heanue et al. |
| 2009/0062844 A1 | 3/2009 | Tekulve et al. |
| 2009/0069885 A1 | 3/2009 | Rahdert et al. |
| 2009/0076541 A1 | 3/2009 | Chin et al. |
| 2009/0088795 A1 | 4/2009 | Cahill |
| 2009/0118745 A1 | 5/2009 | Paul, Jr. |
| 2009/0204133 A1 | 8/2009 | Melzer et al. |
| 2009/0228038 A1 | 9/2009 | Amin |
| 2009/0292310 A1 | 11/2009 | Chin et al. |
| 2009/0306706 A1 | 12/2009 | Osypka |
| 2010/0004679 A1 | 1/2010 | Osypka |
| 2010/0121370 A1 | 5/2010 | Kariniemi |
| 2010/0145382 A1 | 6/2010 | Chanduszko |
| 2010/0234878 A1 | 9/2010 | Hruska et al. |
| 2010/0234884 A1 | 9/2010 | Lafontaine et al. |
| 2010/0234885 A1 | 9/2010 | Frazier et al. |
| 2010/0324538 A1 | 12/2010 | Van Orden |
| 2010/0324585 A1 | 12/2010 | Miles et al. |
| 2010/0324652 A1 | 12/2010 | Aurilia et al. |
| 2011/0040324 A1 | 2/2011 | McCarthy et al. |
| 2011/0054519 A1 | 3/2011 | Neuss |
| 2011/0184439 A1 | 7/2011 | Anderson et al. |
| 2011/0184456 A1 | 7/2011 | Grandfield et al. |
| 2011/0295298 A1 | 12/2011 | Moszner |
| 2011/0301630 A1 | 12/2011 | Hendriksen et al. |
| 2012/0029556 A1 | 2/2012 | Masters |
| 2012/0071918 A1 | 3/2012 | Amin et al. |
| 2012/0143242 A1 | 6/2012 | Masters |
| 2012/0150218 A1 | 6/2012 | Sandgren et al. |
| 2012/0197292 A1 | 8/2012 | Chin-Chen et al. |
| 2012/0245623 A1 | 9/2012 | Kariniemi et al. |
| 2012/0316597 A1 | 12/2012 | Fitz et al. |
| 2013/0041404 A1 | 2/2013 | Amin et al. |
| 2013/0218202 A1 | 8/2013 | Masters |
| 2013/0231684 A1 | 9/2013 | Aurilia et al. |
| 2013/0245666 A1 | 9/2013 | Larsen et al. |
| 2013/0282054 A1 | 10/2013 | Osypka |
| 2013/0296925 A1 | 11/2013 | Chanduszko et al. |
| 2014/0039543 A1 | 2/2014 | Willems et al. |
| 2014/0142610 A1 | 5/2014 | Larsen et al. |
| 2014/0194921 A1 | 7/2014 | Akpinar |
| 2014/0207185 A1 | 7/2014 | Goble et al. |
| 2014/0309684 A1 | 10/2014 | Al-Qbandi et al. |
| 2014/0343602 A1 | 11/2014 | Cox et al. |
| 2015/0005809 A1 | 1/2015 | Ayres et al. |
| 2015/0039023 A1 | 2/2015 | Canniere et al. |
| 2015/0066077 A1 | 3/2015 | Akpinar |
| 2015/0148731 A1 | 5/2015 | McNamara et al. |
| 2015/0196288 A1 | 7/2015 | Van |
| 2017/0035435 A1 | 2/2017 | Amin et al. |

FOREIGN PATENT DOCUMENTS

| | | |
|---|---|---|
| CN | 101460102 A | 6/2009 |
| DE | 9413645 | 10/1994 |
| DE | 9413649 U1 | 10/1994 |
| DE | 102006036649 A1 | 10/2007 |

(56) References Cited

FOREIGN PATENT DOCUMENTS

| | | |
|---|---|---|
| EP | 0362113 | 4/1990 |
| EP | 0474887 | 3/1992 |
| EP | 0839549 | 5/1998 |
| EP | 0861632 | 9/1998 |
| EP | 1013227 | 6/2000 |
| EP | 1046375 | 10/2000 |
| EP | 1222897 | 7/2002 |
| EP | 2340770 A1 | 7/2011 |
| EP | 2524653 A1 | 11/2012 |
| JP | 06-13686 | 4/1994 |
| JP | 10244611 | 9/1998 |
| JP | 2000505668 A | 5/2000 |
| JP | 2000300571 A | 10/2000 |
| JP | 2002513308 A | 5/2002 |
| JP | 2004512153 A | 4/2004 |
| JP | 2004534390 A | 11/2004 |
| JP | 2005521447 A | 7/2005 |
| JP | 2005521818 A | 7/2005 |
| JP | 2005261597 | 9/2005 |
| JP | 2006230800 A | 9/2006 |
| JP | 2007526087 A1 | 9/2007 |
| JP | 2007535986 A | 12/2007 |
| JP | 2009000497 A | 1/2009 |
| JP | 2009512521 A | 3/2009 |
| JP | 2009514624 A | 4/2009 |
| JP | 2009160402 A | 7/2009 |
| JP | 2010525896 A | 7/2010 |
| JP | 2012519572 A | 8/2012 |
| KR | 20010040637 A | 5/2001 |
| RU | 2208400 C2 | 7/2003 |
| RU | 84711 U1 | 7/2009 |
| SU | 1377052 A1 | 2/1988 |
| WO | WO-1993019803 A1 | 10/1993 |
| WO | WO 1996001591 | 1/1996 |
| WO | WO 1996025179 | 8/1996 |
| WO | WO-1996025179 A1 | 8/1996 |
| WO | WO 1996031157 | 10/1996 |
| WO | WO-1996031157 A1 | 10/1996 |
| WO | WO-9640305 | 12/1996 |
| WO | WO 1998007375 | 2/1998 |
| WO | WO-1998007375 A1 | 2/1998 |
| WO | WO 1998008462 | 3/1998 |
| WO | WO 1998016174 | 4/1998 |
| WO | WO 1998029026 | 7/1998 |
| WO | WO 1998051812 | 11/1998 |
| WO | WO 1999005977 | 2/1999 |
| WO | WO 1998018864 | 4/1999 |
| WO | WO 1999018862 | 4/1999 |
| WO | WO 1999018864 | 4/1999 |
| WO | WO 1999018870 | 4/1999 |
| WO | WO 1999018871 | 4/1999 |
| WO | WO 1999030640 | 6/1999 |
| WO | WO-1999039646 A1 | 8/1999 |
| WO | WO 1999066846 | 12/1999 |
| WO | WO 2000027292 | 5/2000 |
| WO | WO 2000044428 | 8/2000 |
| WO | WO-2000051500 A1 | 9/2000 |
| WO | WO 2001008600 | 2/2001 |
| WO | WO-2001017435 A1 | 3/2001 |
| WO | WO 2001019256 | 3/2001 |
| WO | WO 2001021247 | 3/2001 |
| WO | WO 2001028432 | 4/2001 |
| WO | WO 2001030268 | 5/2001 |
| WO | WO 2001049185 | 7/2001 |
| WO | WO-2001072367 A1 | 10/2001 |
| WO | WO 2001078596 | 10/2001 |
| WO | WO 2001093783 | 12/2001 |
| WO | WO 2002017809 | 3/2002 |
| WO | WO 2002024106 | 3/2002 |
| WO | WO-2002038051 A2 | 5/2002 |
| WO | WO 2003001893 | 1/2003 |
| WO | WO 2003024337 | 3/2003 |
| WO | WO 2003053493 | 7/2003 |
| WO | WO-2003053493 A2 | 7/2003 |
| WO | WO 2003059152 | 7/2003 |
| WO | WO-2003061481 A1 | 7/2003 |
| WO | WO 2003063732 | 8/2003 |
| WO | WO 2003077733 | 9/2003 |
| WO | WO 2003082076 | 10/2003 |
| WO | WO 2003103476 | 12/2003 |
| WO | WO-2004012603 A2 | 2/2004 |
| WO | WO 2004032993 | 4/2004 |
| WO | WO 2004037333 | 5/2004 |
| WO | WO 2004043266 | 5/2004 |
| WO | WO 2004043508 | 5/2004 |
| WO | WO 2004052213 | 6/2004 |
| WO | WO-2004067092 A2 | 8/2004 |
| WO | WO-2004101019 A2 | 11/2004 |
| WO | WO 2005006990 | 1/2005 |
| WO | WO 2005018728 | 3/2005 |
| WO | WO-2005018728 A2 | 3/2005 |
| WO | WO 2005027752 | 3/2005 |
| WO | WO-2005032335 A2 | 4/2005 |
| WO | WO-2005034724 A2 | 4/2005 |
| WO | WO 2005074813 | 8/2005 |
| WO | WO 2005092203 | 10/2005 |
| WO | WO 2005110240 | 11/2005 |
| WO | WO 2005112779 | 12/2005 |
| WO | WO 2006036837 | 4/2006 |
| WO | WO-2006041612 A2 | 4/2006 |
| WO | WO-2006062711 A2 | 6/2006 |
| WO | WO 2006102213 | 9/2006 |
| WO | WO-2007124862 A2 | 11/2007 |
| WO | WO-2007140797 A1 | 12/2007 |
| WO | WO-2008125689 A1 | 10/2008 |
| WO | WO-2008137603 A2 | 11/2008 |
| WO | WO-2008153872 A2 | 12/2008 |
| WO | WO-2008156464 A1 | 12/2008 |
| WO | WO-2012003317 A1 | 1/2012 |

OTHER PUBLICATIONS

European Search Report, European Application No. 11007412.7, dated Jan. 19, 2012, 5 pages.
International Preliminary Report on Patentability and Written Opinion for PCT/US2010/039354 dated Jan. 4, 2012, 5 pages.
International Preliminary Report on Patentability and Written Opinion for PCT/US2010/039358 dated Jan. 4, 2012, 7 pages.
International Preliminary Report on Patentability and Written Opinion for PCT/US2009/004307, dated Sep 13, 2011, 8 pages.
International Preliminary Report on Patentability for PCT/US2012/063598, dated May 13, 2014, 7 pages.
International Search Report and Written Opinion for PCT/US2014/011980, dated Sep. 9, 2014, 32 pages.
International Search Report and Written Opinion for PCT/US2014/017129 dated May 14, 2014, 9 pages.
International Search Report and Written Opinion; dated Feb. 22, 2013; World Intellectual Property Organization (WIPO) (International Bureau of); PCT/US2012/050358; 15 pages.
International Search Report for PCT/US2009/004307, dated Nov. 27, 2009, 6 pages.
International Search Report for PCT/US2010/039354, dated Sep. 15, 2010, 5 pages.
International Search Report for PCT/US2010/039358 dated Sep. 3, 2010, 5 pages.
International Search Report for PCT/US2012/050785, dated Nov. 23, 2012, 6 pages.
International Search Report, International Application No. PCT/US03/35998 dated Jun. 16, 2004 (5 pgs}.
International Search Report, International Application No. PCT/US03/39253, dated Apr. 19, 2004 (4 pgs).
International Search Report, International Application No. PCT/US04/022643, dated Mar. 31, 2005 (2 pgs).
International Search Report, International Application No. PCT/US04/029978, dated Jan. 26, 2005 (3 pgs).
Schaffer and Gordon, "Engineering Characteristics of Drawn Filled Nitinol Tube" SMST-2003: Proceedings of the International Conference on Shape Memory and Superelastic Technologies (ASM International), pp. 109-118, 2004.

(56) References Cited

OTHER PUBLICATIONS

Athanasion, "Coronary artery bypass with the use of a magnetic distal anastomotic device: surgical technique and preliminary experience," *Heart Surg Forum.*, 2004;7(6):356-359.
Bachthaler, "Corrosion of tungsten coils after peripheral vascular embolization therapy: influence on outcome and tungsten load," *Catheter Cardiovasc Interv.*, Jul. 2004;62(3):380-384.
Falk, "Facilitated endoscopic beating heart coronary artery bypass grafting using a magnetic coupling device," *J Thorac Cardiovasc Surg.*, 126(5):1575-1579, Nov. 2003.
Filsoufi et al., "Automated distal coronary bypass with a novel magnetic coupler (MVP system)," *J Thorac Cardiovasc Surg.*, Jan. 2004;127(1):185-192.
Isotalo et al., "Biocompatibility testing of a new bioabsorbable X-ray positive SR-PLA 96/4 urethral stent," *J Urol.*, Nov. 1999;162(5):1764-1767.
Jackson et al., "55-nitinol—the alloy with a memory—its physical metallurgy, properties and applications," *NASA*, pp. 24-25, 1972.
Kilma, "Magnetic Vascular Port in minimally invasive direct coronary artery bypass grafting," *Circulation*, Sep. 14, 2004;110(11 Suppl 1):II55-60.
Kimura, A., et al., "Effects of Neutron Irradiation on the Transformation Behavior in Ti—Ni Alloys," Abstract, Proceedings of the Int'l Conf. on Marienstic Transformations, 1992, pp. 935-940.
Meier and Lock, "Contemporary management of patent foramen ovale," *Circulation.*, Jan. 7, 2003;107(1):5-9.
Parviainen et al., "A new biodegradable stent for the pancreaticojejunal anastomosis after pancreaticoduodenal resection: in vitro examination and pilot experiences in humans," *Pancreas.*, Jul. 2000;21(1):14-21.
Ramanathan, G., et. al., "Experimental and Computational Methods for Shape Memory Alloys," 15th ASCE Engineering Mechanics Conference, Jun. 2-5, 2002.
Ruddy and McNally, "Rheological, Mechanical and Thermal Behaviour of Radiopaque Filled Polymers," ANTEC Papers: 2005, Polymer Processing Research Centre, School of Chemical Engineering, Queen's University of Belfast, Belfast UK, pp. 167-171, 2005.
Ruiz, et al., "The puncture technique: A new method for transcatheter closure of patent foramen ovale," *Catheterization and Cardiovascular Interventions*, 2001, vol. 53, pp. 369-372.
Shabalovskaya, "Surface, corrosion and biocompatibility aspects of Nitinol as an implant material," *Biomed Mater Eng.*, 2002;12(1):69-109.
SMST-2000, "Proceedings of the International Conference on Shape Memory and Superelastic Technologies," Apr. 30 to May 4, 2000, Asilomar Conference Center.
Stein, H., "Telemanipulator-gestutzte Applikation eines magnetischen Gefa.beta.-Kopplers am schlagenden Herzen mit dem da Vinci.TM.—Surgical-System," [Telemanipulatory Application of a Magnetic Vascular Coupler on the Beating Heart with the da Vinci TM surgical system.] Biomedizinische Technik, 2003, vol. 48(9), pp. 230-234. [English abstract].
Stockel, "Nitinol Medical Devices and Implants," SMST-2000 Conference Proceedings, 2001, pp. 531-541.
Uchil, "Shape Memory Alloys—Characterization Techniques," *Pramana—Journal of Physics*, 2002 vol. 58 (5)(6), pp. 1131-1139.
Vaajanen et al., "Expansion and fixation properties of a new braided biodegradable urethral stent: an experimental study in the rabbit," *The Journal of Urology, J Urol.*, Mar. 2003;169(3):1171-1174.
European Examination Report, European Application No. 03729663.9, dated Jul. 16, 2008 (5 Pages).
European Examination Report, European Application No. 03731562.9, dated Jul. 18, 2008 (3 Pages).
European Examination Report, European Application No. 03779297.5, dated Mar. 15, 2007 (6 Pages).
European Examination Report, European Application No. 04781644.2, dated Aug. 23, 2007 (3 Pages).
European Search Report, European Application No. 03729663.9, dated Feb. 20, 2008 (3 Pages).
International Search Report and Written Opinion, International Patent Application No. PCT/US06/41255, dated Jun. 13, 2008 (6 pgs).
International Search Report and Written Opinion, International Patent Application No. PCT/US08/59429, dated Sep. 5, 2008 (9 pgs).
International Search Report for International Patent Application No. PCT/AU03/00759, dated Jun. 19, 2003.
International Search Report, International Application No. PCT/US02/40850 dated Jun. 19, 2003 (4 pgs).
International Search Report, International Application No. PCT/US03/01050, dated Jul. 8, 2003 (1 pg).
International Search Report, International Application No. PCT/US03/09051, dated Sep. 29, 2003 (2 pgs).
International Search Report, International Application No. PCT/US03/17390 dated Oct. 6, 2003 (4 pgs).
International Search Report, International Application No. PCT/US03/17715, dated Mar. 24, 2004 (2 pgs).
International Search Report, International Application No. PCT/US03/32133, dated Apr. 22, 2004 (1 pg).
International Search Report, International Application No. PCT/US03/34003 dated Oct. 3, 2004 (4 pgs).
International Search Report, International Application No. PCT/US03/35479, dated Apr. 14, 2004 (2 pages).
International Search Report, International Application No. PCT/US04/026998, dated Apr. 22, 2005 (5 pgs).
International Search Report, International Application No. PCT/US05/006703, dated Jul. 25, 2005 (3 pgs).
International Search Report, International Application No. PCT/US05/013705 dated Aug. 4, 2005 (4 pgs).
International Search Report, International Application No. PCT/US05/015382, dated Oct. 6, 2005 (4 pgs).
International Search Report, International Application No. PCT/US05/34276, dated Oct. 9, 2007.
International Search Report, International Application No. PCT/US06/009978, dated Jul. 13, 2006 (2 pgs).
International Search Report, International Application No. PCT/US07/065546, dated Oct. 29, 2007. 4 pages.
International Search Report, International Application No. PCT/US2007/065526, dated Aug. 8, 2007 (5 pgs).
International Search Report, International Application No. PCT/US2007/065541, dated Aug. 7, 2007 (4 pgs).
International Search Report, International Application No. PCT/US97/14822, dated Feb. 20, 1998 (2 pgs).
International Search Report, International Application No. PCT/US97/17927, dated Feb. 10, 1998 (1 pg).
European Search Report, European Application No. 12150504.4, dated Jul. 2, 2012, 5 pages.
International Preliminary Report on Patentability issued in PCT/US2015/034452, dated Dec. 15, 2016, 10 pages.
International Search Report and Written Opinion for PCT/US2012/063598, dated Feb. 4, 2013, 11 pages.

* cited by examiner

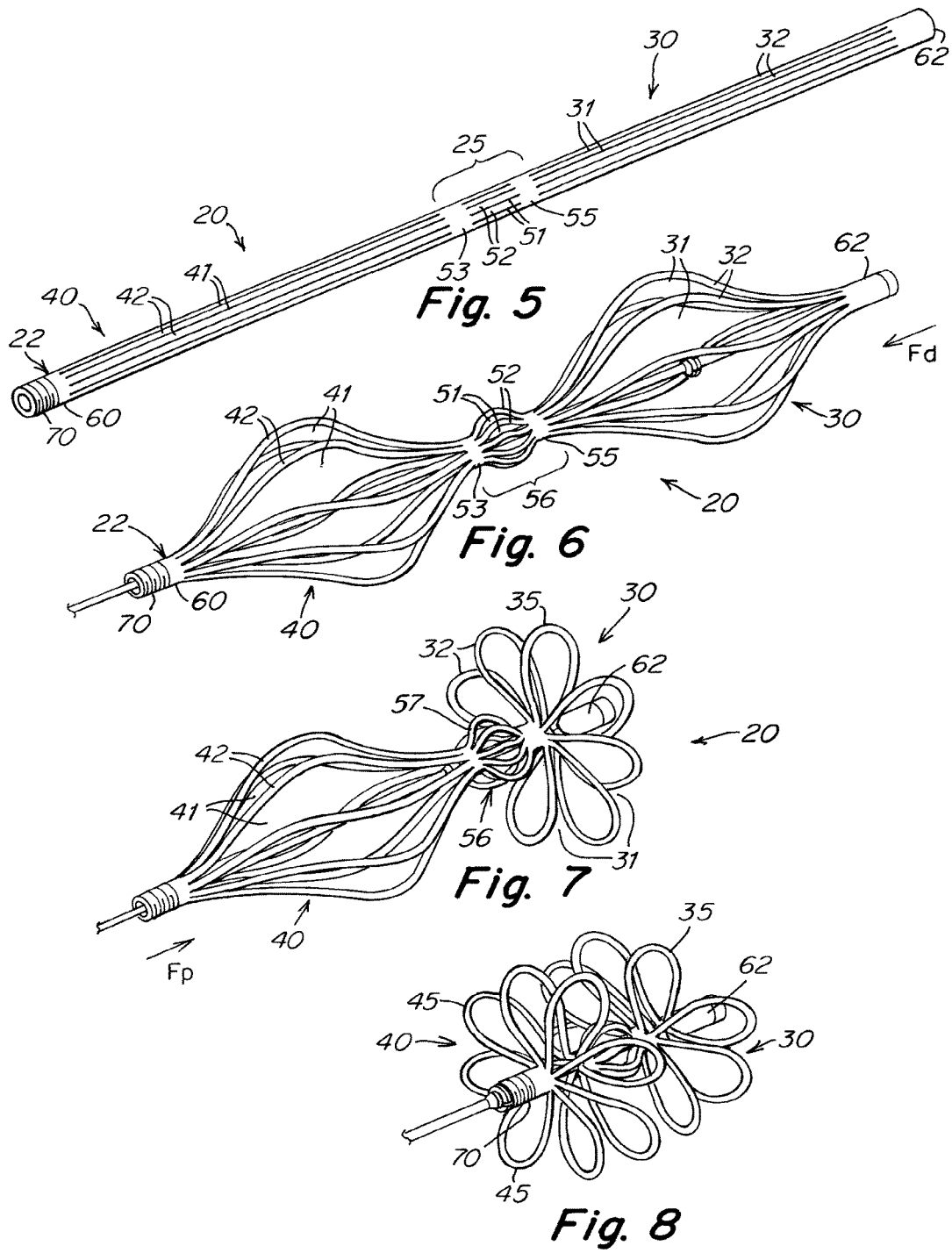

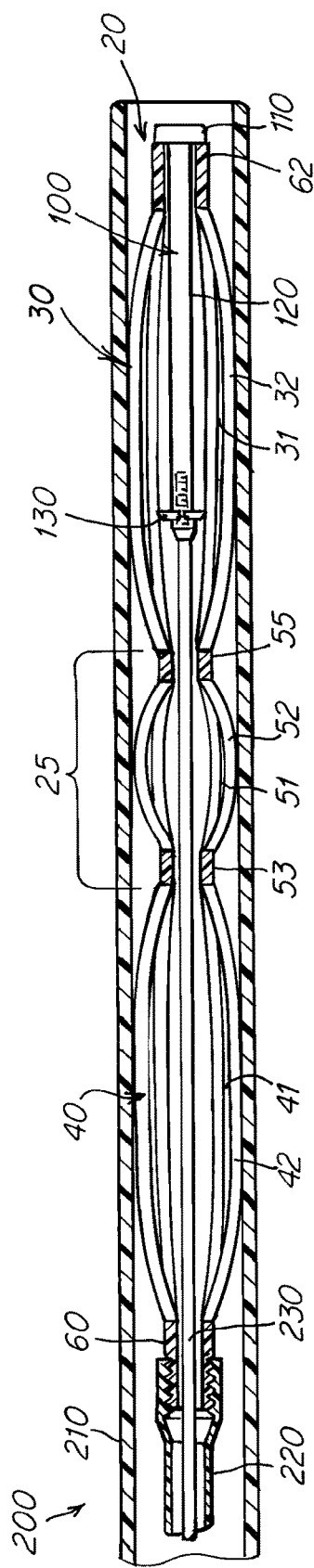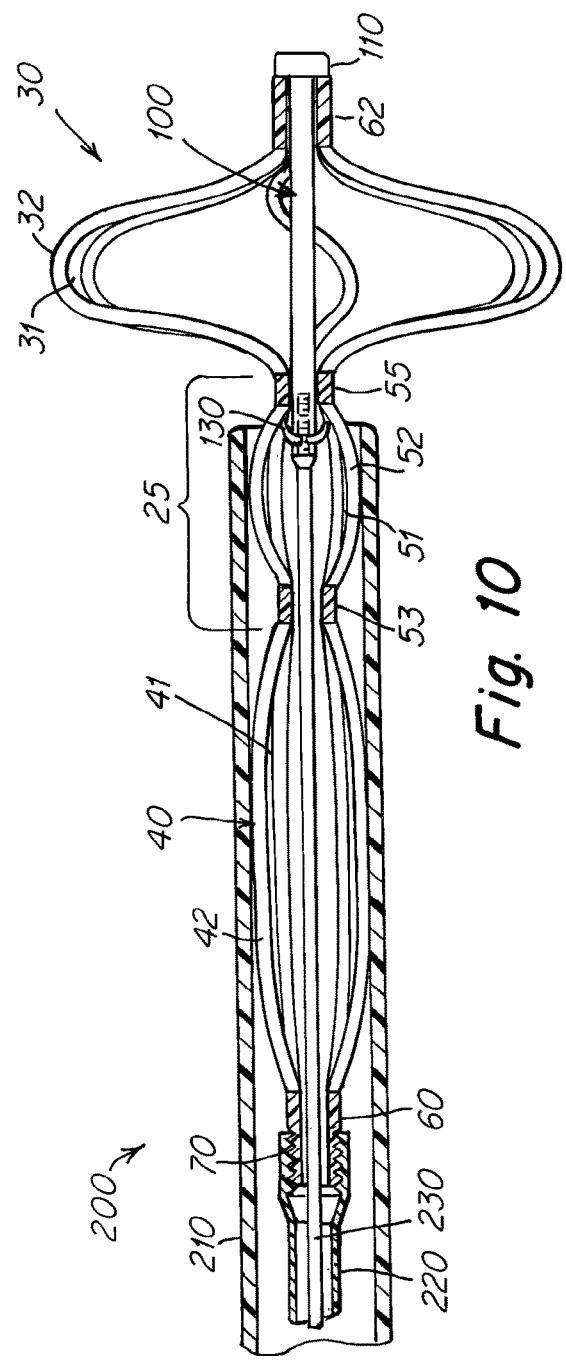

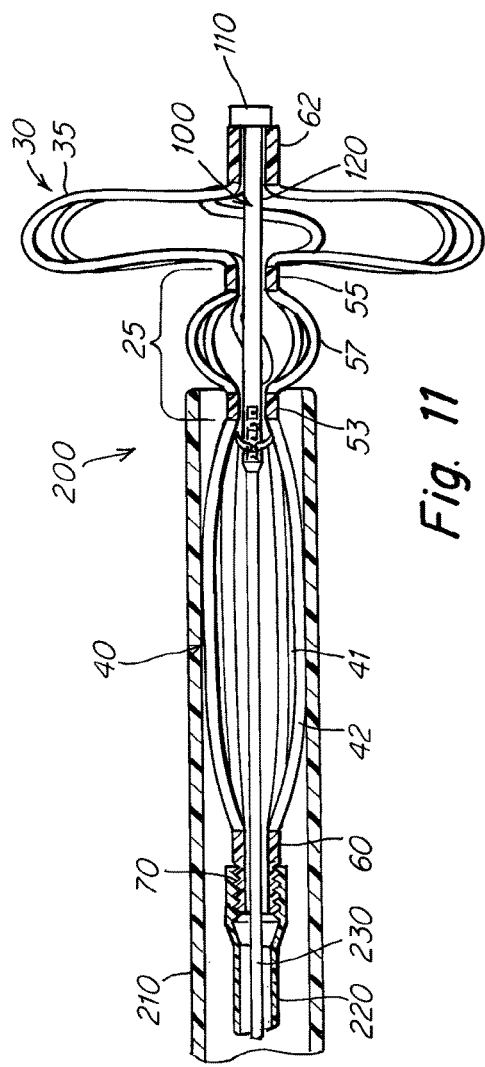
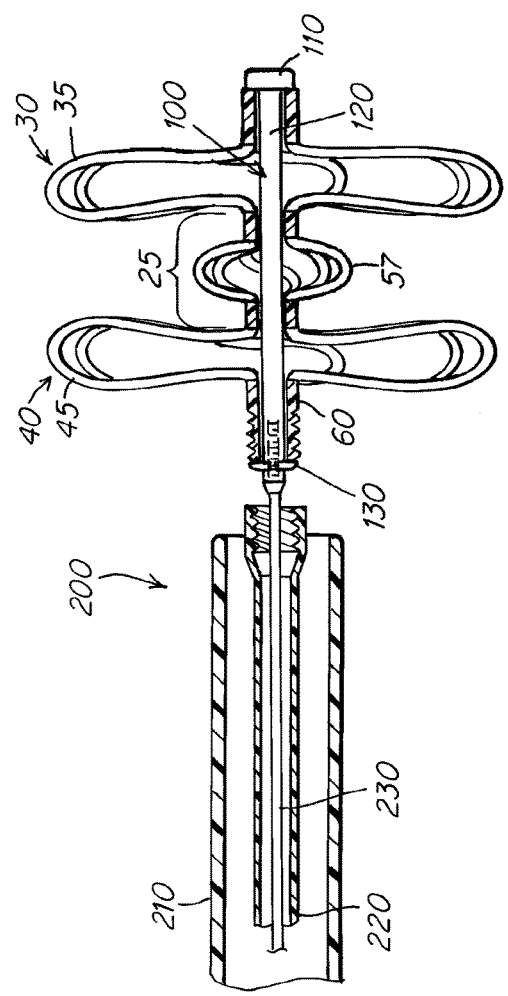
Fig. 11
Fig. 12

SEPTAL CLOSURE DEVICE WITH CENTERING MECHANISM

CROSS-REFERENCE TO RELATED APPLICATIONS

This application is a Continuation of application Ser. No. 12/062,904, filed Apr. 4, 2008, which claims the benefit under 35 U.S.C. § 119(e) to U.S. Provisional Patent Application No. 60/921,969, entitled Septal Closure Device With Centering Mechanism, filed Apr. 5, 2007, the contents of which are incorporated by reference herein.

BACKGROUND OF THE INVENTION

Field of the Invention

The invention relates generally to occlusion devices for closing physical anomalies, such as an atrial septal defect, a patent foramen ovale, and other septal and vascular defects.

Description of Related Art

A patent foramen ovale (PFO), illustrated in FIG. 1, is a persistent, one-way, usually flap-like opening in the wall between the right atrium 11 and left atrium 13 of the heart 10. Because left atrial (LA) pressure is normally higher than right atrial (RA) pressure, the flap usually stays closed. Under certain conditions, however, right atrial pressure can exceed left atrial pressure, creating the possibility that blood could pass from the right atrium 11 to the left atrium 13 and blood clots could enter the systemic circulation. It is desirable that this circumstance be eliminated.

The foramen ovale serves a desired purpose when a fetus is gestating in utero. Because blood is oxygenated through the umbilical chord, and not through the developing lungs, the circulatory system of the fetal heart allows the blood to flow through the foramen ovale as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two over-lapping layers of tissue: septum primum 14 and septum secundum 16. However, a PFO has been shown to persist in a number of adults.

The presence of a PFO is generally considered to have no therapeutic consequence in otherwise healthy adults. Paradoxical embolism via a PFO is considered in the diagnosis for patients who have suffered a stroke or transient ischemic attack (TIA) in the presence of a PFO and without another identified cause of ischemic stroke. While there is currently no definitive proof of a cause-effect relationship, many studies have confirmed a strong association between the presence of a PFO and the risk for paradoxical embolism or stroke. In addition, there is significant evidence that patients with a PFO who have had a cerebral vascular event are at increased risk for future, recurrent cerebrovascular events. The presence of a PFO has also been linked to chronic migraine headaches. Although researchers are still investigating an explanation for the link, PFO closure has been shown to eliminate or significantly reduce migraine headaches in many patients In certain cases, such as when anticoagulation is contraindicated, surgery may be necessary or desirable to close a PFO. The surgery would typically include suturing a PFO closed by attaching septum secundum to septum primum. This sutured attachment can be accomplished using either an interrupted or a continuous stitch and is a common way a surgeon shuts a PFO under direct visualization.

An atrial septal defect (ASD) is a defect in the septal wall of the heart between the heart's two upper chambers (the atria), and a ventricular septal defect (VSD) is a defect in the septal wall between the heart's two lower chambers (the ventricles). Septal defects of this type are sometimes referred to as a "hole" in the heart. Meanwhile, a patent ductus arteriosus (PDA) is a persistent opening between the aorta and the pulmonary artery. While this connection is normal for a fetus gestating in utero, if the opening fails to close soon after birth, the opening can allow blood to flow directly from the aorta into the pulmonary artery, which can put strain on the heart and increased the blood pressure in the lung arties.

Umbrella devices and a variety of other similar mechanical closure devices have been developed for percutaneous closure of the defects described above. However, because of the unique geometries of each type of defect (e.g., PFO, ASD, VSD, or PDA), devices intended for one type of defect may not be optimally suited for use in another type of defect. Moreover, adapting a device developed for one type of defect to another type of defect may present certain challenges. Even if a device developed for a particular type of defect can be deployed within a defect of another type, some components of the device may insecurely seat against the septum and, thereby, risking thrombus formation due to hemodynamic disturbances.

In some cases, the size of the aperture is greater than the size of the center portion or other closure feature of the device. Upon deployment, such a device can slide toward one side within the aperture and thus occlude only one side or portion of the defect and result in a leak on the other side. Finally, some septal closure devices are complex to manufacture, which may result in inconsistent product performance.

The presently disclosed embodiments are designed to address these and other deficiencies of prior art septal closure devices.

BRIEF SUMMARY OF THE INVENTION

In one aspect, the present invention provides a device for occluding an aperture in the septum, including a first side adapted to be disposed on one side of the septum and a second side adapted to be disposed on the opposite side of the septum. The device has an elongated, low-profile delivery configuration and a shortened, higher-profile deployment configuration. The first and second sides are adapted to occlude the aperture upon deployment of the device at its intended delivery location. The device also includes a radially expandable center portion. The device can be secured in the deployed configuration using a catch system.

In one aspect, the device is formed from a tubular body. Slits or openings are provided in the tubular body, either be cutting or by selectively bonding structural members such as filaments to define the body. In some embodiments, axially extending slits evenly distributed around the circumference of the distal portion of the tube define distal struts and axially extending slits evenly distributed around the circumference of the proximal portion of the tube define proximal struts. The distal and proximal struts form loops in the deployed configuration. In some embodiments, the loops cover the sides of the aperture or provide a compressive force to the septal tissue surrounding the aperture or both. A center portion connects the distal side and the proximal side of the occluder and extends through the aperture when deployed. Axially extending slits evenly distributed around the circumference of the center portion of the tube further define struts that expand radially to form ribs in the deployed configuration. The ribs provide an expandable center portion. The expandable center portion is separated from the distal loops by a distal joint and from the proximal loops by a proximal joint. The expandable center portion positions and/or secures the device in the aperture, prevents the device from shifting to one side, and prevents leaks. Accordingly, the expandable center portion provides a self-centering mechanism.

The expandable center portion may include the same number or a different number of struts than the distal and/or proximal portions of the occluder. In some embodiments, the expandable center portion when expanded has a smaller diameter measured transverse to the axis of the tube than the distal or proximal loops. The ribs of the expandable center portion also are curved less sharply than the distal or proximal loops.

The tubular body may include a material selected from metals, shape memory materials, alloys, polymers, bioabsorbable polymers, and combinations thereof. In particular embodiments, the tubular body includes a shape memory polymer.

In another aspect, an occluder is formed by providing a first plurality of axially-extending slits in a proximal portion, a second plurality of axially-extending slits in a center portion, and a third plurality of axially-extending slits in a distal portion.

In accordance with another aspect, an occluder is provided that is adapted to be introduced into a body through a vasculature. The occluder includes a tube with a proximal side and a distal side that cooperate to close the defect. The occluder also has a central portion disposed between the proximal side and the distal side. The central portion is operable to expand when an axial length of the occluder is shortened. The tube includes slits to provide struts that are joined at the central portion, wherein the struts form loops when the axial length of the tube is shortened. In one aspect, the slits may comprise a first plurality of axially-extending slits in the proximal side, a second plurality of axially-extending slits in the central portion, and a third plurality of axially-extending slits in the distal side. A first uncut portion of the tube may provide a proximal joint, and a second uncut portion of the tube may provide a distal joint, such that the distal and proximal joints are configured to maintain a tubular profile upon a transformation of the occluder to a deployed configuration.

In another with a further aspect, the loops are formed at the proximal side and the distal side of the occluder, and when the occluder is subjected to a compressive force, the loops form curves extending to convergence areas that connect adjacent struts at distal and proximal ends of the central portion, such that the central portion expands uniformly in a radial direction, so that the occluder is self centered when disposed in the defect. The locations of the convergence areas may alternate in a circumferential direction of the central portion between the distal end of the central portion and the proximal end of the central portion.

In another aspect, provided is a method for deploying an occluding member having a series of loops formed by struts in a tube, the struts being formed by a series of offset slits which are configured to form proximal side loops and distal side loops that are coupled to each other by a central portion of the tube, such that when an axial length of the tube is shortened, the proximal side loops and the distal side loops extend radially outwardly. A delivery system is inserted into a lumen of a body for delivering the occluder; and a distal part of the occluder is deployed so that the distal side loops expand to be disposed along a surface around a defect to be occluded. A catch element is moved through an axially central passage of the occluder until the catch element engages an area between the distal side loops and the central portion to hold the distal part of the device in a deployed state. The central portion of the occluder is deployed so that the central portion is expanded within an aperture of the defect. The axial length of the occluder is shortened by moving the catch element through the axially central passage of the occluder until the catch element engages an area between the central portion and the proximal side loops. A proximal part of the occluder is then deployed so that the proximate side loops are disposed along a second surface around the defect to be occluded, and the catch element is moved through the axially central passage of the occluder until the catch element engages a proximal end of the occluder.

BRIEF DESCRIPTION OF THE SEVERAL VIEWS OF THE DRAWINGS

FIGS. 5-8 are isometric views of an embodiment of an occluder according to an exemplary embodiment of the present invention;

FIGS. 9-12 are schematic views of a deployment sequence for an occluder according to an embodiment of the invention;

DETAILED DESCRIPTION

Embodiments consistent with the present invention provide a device for occluding an aperture within body tissue. This device relates particularly to, but is not limited to, a septal occluder made from a polymer tube. In particular and as described in detail below, the occluder of the present invention may be used for closing an ASD, ventricular septal defect (VSD) or PFO in the atrial septum of a heart. Although the embodiments of the invention are described with reference to an ASD, VSD or PFO, one skilled in the art will recognize that the device and methods of the present invention may be used to treat other anatomical conditions. As such, the invention should not be considered limited in applicability to any particular anatomical condition.

Figure 1:
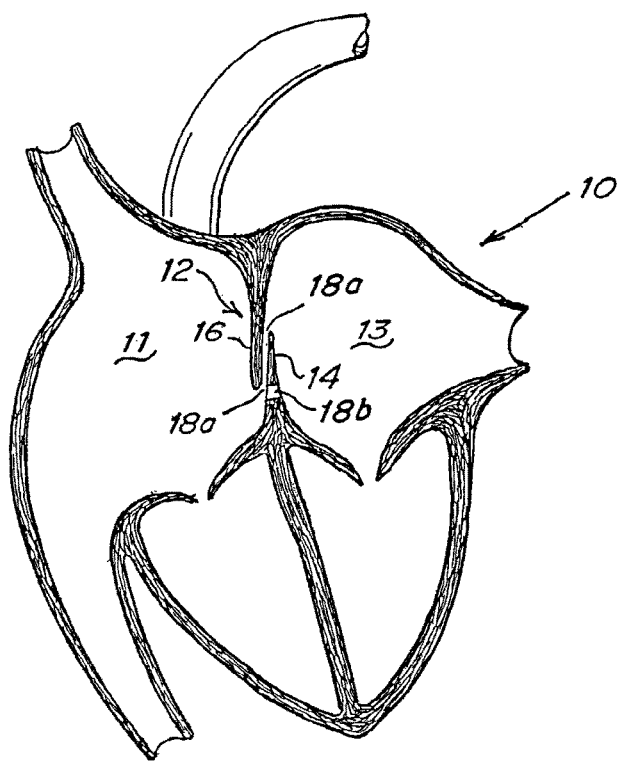
FIG. 1 is a schematic representation of a human heart including various septal defects.

FIG. 1 illustrates a human heart 10, having a right atrium 11 and a left atrium 13 and including various anatomical anomalies 18a and 18b. The atrial septum 12 includes septum primum 14 and septum secundum 16. The anatomy of the septum 12 varies widely within the population. In some people, septum primum 14 extends to and overlaps with septum secundum 16. The septum primum 14 may be quite thin. When anatomical anomalies are present, blood could travel through the passage 18a (referred to as "the PFO tunnel") or 18b (referred to as an ASD) between septum primum 14 and septum secundum 16.

The term "bioabsorbable," as used in this application, is also understood to mean "bioresorbable."

In this application, "distal" refers to the direction away from a catheter insertion location and "proximal" refers to the direction nearer the insertion location.

Figure 2:
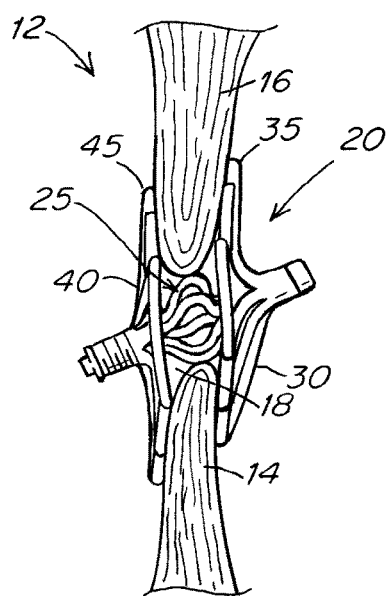
FIG. 2 is view of an occluder deployed in the heart of a patient according to an embodiment of the invention.
Figure 3:
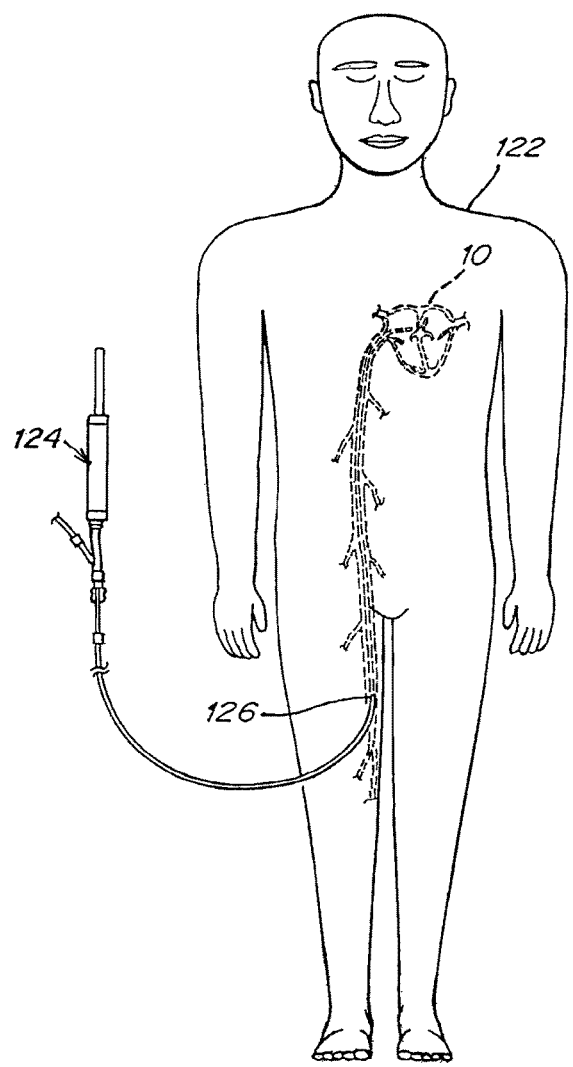
FIG. 3 is a schematic representation of the introduction of a catheter containing an occluder to the body of a patient.
Figure 4:
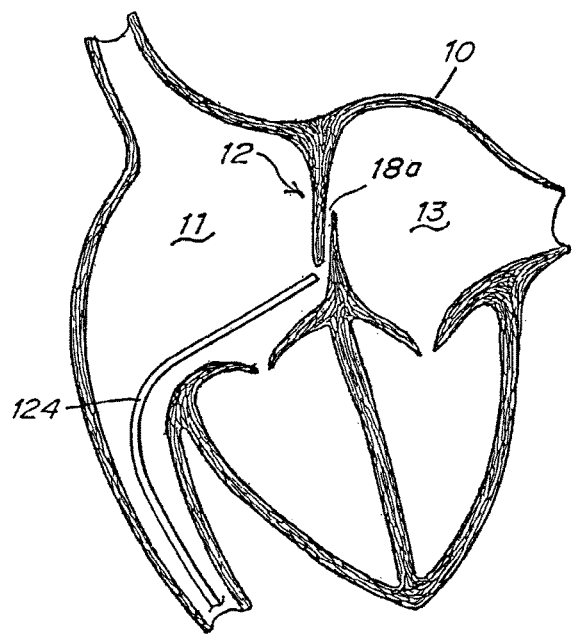
FIG. 4 is a schematic representation of the introduction of a catheter containing an occluder according to an embodiment of the invention to a deployment site within the heart.

FIG. 2 illustrates an embodiment of an occluder 20 according to one aspect of the invention, deployed in a heart. The occluder 20, has a distal side 30 and a proximal side 40, disposed on respective sides of the aperture 18. The distal side 30 and the proximal side 40 include features that cooperate to close the aperture 18, and, in certain embodiments, provide compressive force to hold the aperture 18 closed. Referring to occluder 20, distal side 30 and proximal side 40 are connected by central portion 25. The occluder 20 may be inserted into the septal tissue 12 to prevent the flow of blood through the aperture 18, e.g., such that the distal side 30 is located in the left atrium 13 and the proximal side 40 is located in the right atrium 11. The central portion 25 is substantially disposed within aperture 18. Additionally or alternatively, the occluder 20 may be inserted into the septal tissue so as to prevent the flow of blood through the aperture 18, e.g., the occluder may extend through the septum primum and septum secundum such that the distal side 30 is located in the left atrium 13 and the proximal side 40 is located in the right atrium 11. As used in this application, unless otherwise indicated, the term "aperture 18" refers to any anatomical anomaly that may be treated by use of occluder 20, such as PFO 18a, ASD 18b, VSD (not shown), and/or PDA (not shown). FIG. 3 illustrates use of a catheter system 124, which can be externally manipulated by a clinician, by insertion of a portion of catheter system 124 into a patient's body 122 at a catheter insertion point 126 to deliver occluder 20. The distal end of the delivery assembly 124 is advanced toward and into the heart 10 until the distal end is in proximity to the defect to be closed. FIG. 4 illustrates a detail view of the introduction of catheter system 124 into the heart.

Referring now also to FIGS. 5-8, providing perspective views of the occluder 20, in the illustrated embodiment, the occluder 20 is constructed of one or more metal or polymer tube(s) or filaments, forming a body referred to collectively as tube 22. Tube 22 includes slits 31 and 41 and 51, which in some embodiments are formed using an etching or cutting process that produces a particular cutting pattern on the tube 22. Other embodiments include slits formed by providing openings wherein adjacent filaments are not bonded. Slits 31 are of equal length, are radially even spaced and are disposed parallel to the axis of the tube 22. For example, the slits 31 are cut along the axial length of the upper half of the tube 22 using a cutting tool, e.g., a razor blade. According to some exemplary embodiments of the present invention the slits 31 are cut without removing any significant amount of material from tube 22, i.e., the formation of the slits 31 does not significantly reduce the overall volume of the tube 22. According to other embodiments of the present invention, the slits 31 are formed by cutting material out of the tube 22 such that the volume of the tube 22 is reduced. Both ends of each of slits 31 may be rounded so as to relieve stresses at the axial ends of the slits 31. This helps prevent the slits 31 from lengthening due to cyclic stresses present in a beating heart and the resultant material fatigue. In those embodiments where the slits 31 are formed by cutting material out of the tube 22, the slits 41 and 51 are similarly formed.

An uncut portion of tube 22 between slits 41 and 51 provides a proximal joint 53, and an uncut portion of tube 22 between slits 31 and 51 provides a distal joint 55. In addition, the proximal end 60 and the distal end 62 of the tube are also not cut. In the cut segments, slits 31, 41 and 51 define a plurality of struts, respectively 32, 42 and 52. The occluder 20 is transformable from a delivery configuration to a deployed configuration. FIG. 5 closely approximates the delivery configuration of the occluder 20. The transformation is represented in FIGS. 5-8, and the fully deployed condition, in a human heart, is illustrated in FIG. 2. The occluder 20 can be delivered via a catheter assembly such as catheter system 124 and has a tubular delivery configuration well-suited to delivery via a catheter assembly. The deployed configuration is attained by shortening the axial length of the tube 22 and securing the occluder 20 in that configuration. Distal and proximal struts 32 and 42 form loops 35 and 45 respectively in the occluder 20 in the deployed configuration. The center struts 52 form curved ribs 57 that provide an expanding center portion 56 in the deployed configuration. The deployed configuration and deployment techniques are discussed further below.

The shape of the occluder 20 in the deployed configuration is determined by the cutting pattern on tube 22. For example, and as shown in FIG. 8, petal-shaped loops 35 and 45 are produced by cutting slits 31 in the distal side 30 of tube 22, and cutting slits 41 in the proximal side 40 of tube 22 according to the cutting pattern shown in FIG. 5. As shown in FIG. 5, the distal side 30 of tube 22 includes eight cuts 31, extending longitudinally and equally spaced apart around the circumference of the tube 22. Upon application of force $F_d$ to end 62 to shorten the axial length of distal portion 30, struts 32 bow and twist outward to form petal-shaped loops 35 in distal side 30. The movement of the struts 31 during deployment is such that the struts rotate in an orthogonal plane relative to the axis of the device. Center portion 25 may be constrained during the application of force $F_d$, or any combination of forces sufficient to reduce the axial length of the distal portion of the tube 22 may be applied to achieve this effect. One end of each of petal-shaped loops 35 originates from center portion 25, while the other end originates from distal end 62. Petal-shaped loops 45 may be formed in proximal side 40 of tube 22 using the same cutting pattern described above.

The slits 51 provided in the center portion 25 also define struts 52. Struts 52 similarly bend outward when the tube 22 is compressed in the axial direction. Unlike struts 32 and 42, struts 52 are not designed to bow and twist outward forming petal-like loops; instead, struts 52 curve outward, forming curved ribs 57, shortening the axial length of center portion 25 and widening the radius of center portion 25. The slits 51 are shorter than the slits 41 and 31, forming shorter struts. Ribs 57 have a gentler curve and incorporate low strain bends relative to the distal and proximal loops 35 and 45. In some embodiments, the expanded radius of the center portion 25 is less than the expanded radius of loops 35 and 45. In the illustrated embodiments, eight slits 51 are provided in the center portion 25 of the occluder 20. Although here the number of slits 51 is the same as the number of slits 31 in the distal side and the number of slits 41 in the proximal side, different numbers of slits 51 can be provided in center portion 25 and the number of slits can be different from the proximal side 40 and distal side 30.

Given that the surface of occluder 20 will contact septal tissue 12 once it is deployed in vivo, slits 31 and 41 and 51 are cut so as to prevent the formation of sharp, potentially damaging edges along their length. For example, a heated cutting tool may be used to cut slits 31 and 41 and 51 such that the material of tube 22 melts slightly when placed in contact with the cutting tool. Such melting rounds the edges of the sections. Lasers may also be used to cut slits 31 and 41 and 51. According to this process, the edges of loops 32 and 42 formed by the cutting of slits 31 and 41 and 51 are blunted (due to melting) to prevent tissue damage in vivo.

The distal side 30 of the occluder 20 (also called the "anchor portion") includes eight loops (collectively referred to as loops 35). As previously described, each of loops 35 are formed by corresponding cut sections forming struts 32, produced by cutting slits 31. The application of force $F_d$ to distal end 62 of tube 22 brings the axial ends of slits 31 together such that struts 32 bow and twist outwardly to form loops 35 of distal side 30. Central portion 25, or more particularly distal joint 55, may be constrained during the application of force $F_d$. One skilled in the art will recognize that any combination of forces sufficient to reduce the axial length of the tube 22 would be sufficient to deploy the distal side 30 of occluder 20.

As illustrated, the loops 35 are evenly distributed about the tube 22 and end 62. Thus, when the distal side 30 includes eight loops 35, the eight slits 31 are spaced 45 degrees radially apart. Similarly, when the distal side 30 includes six loops 32, the six slits 31 are spaced 60 degrees radially apart. The angle between radially equally-spaced loops is determined by the formula $(360/n_d)$, where $n_d$ is the total number of loops 32.

Although the distal side 30 of the occluder 20 eight loops 35, occluders according to an exemplary embodiment of the present invention may include any number of loops 35 necessary for a given application. In particular embodiments, the distal side 30 of occluder 20 includes six loops 35. Occluders having between four and ten loops 35 may be formed without requiring significant adjustments in the processes described in this application. However, occluders having less than four or more than ten loops 35 may be complicated to manufacture and difficult deliver through the vasculature.

Regardless of the number of loops 35 included in distal side 30 and depending upon the material used to form occluder 20, the outer perimeter of loops 35 may vary. In some embodiments, the loops on one side are of equal diameter. In at least some embodiments, the outer perimeter of loops 35 is rounded to provide an occluder 20 having a smooth, circular perimeter. As the number of loops 35 in the distal side 30 of occluder 20 increases, it becomes desirable to round the outer perimeters of the loops 35 so as to prevent the infliction of trauma on the surrounding septal tissue 12. The outer perimeter of the loops 35 may bend inwardly more than inner portions of the loops 35 to provide a force distribution that helps secure the occluder 20 in place.

The proximal side 40 of the occluder 20 also includes eight loops (collectively referred to as loops 45). As previously described, each of loops 45 are formed by corresponding cut sections forming struts 42, produced by cutting slits 41. The application of force $F_p$ to proximal end 60 of tube 22 brings the axial ends of slits 41 together such that struts bow and twist outwardly to form loops 45 of proximal side 40. Central portion 25, or more particularly proximal joint 53, may be constrained during the application of force $F_p$. One skilled in the art will recognize that any combination of forces sufficient to reduce the axial length of the tube 22 would be sufficient to deploy the proximal side 40 of occluder 20. As described above for distal loops 35, the loops 45 are evenly distributed about central portion 25. Similarly, the angle between radially equally-spaced slits 41 in the proximal side 40 is determined by the formula $(360/n_d)$, where $n_d$ is the total number of loops 45.

Although the proximal side 40 of the occluder 20 has eight loops 45, one skilled in the art will recognize that the proximal side 40 of an occluder according to the present invention may include any number of loops 45 required and suitable for a given application. In particular embodiments, the proximal side 40 of occluder 20 includes six loops 45. Further, although as illustrated, distal side 30 and proximal side 40 both include eight loops, there is no requirement that distal side 30 and proximal side 40 of occluder 20 include the same number of loops. In fact, in particular applications, it may be advantageous to use an occluder 20 in which the distal side 30 contains fewer loops than the proximal side 40, or vice versa.

It will be apparent to one skilled in the art that loops 35 and loops 45 do not have to be the same size, although they could be. In one embodiment, loops 35 are larger in size than loops 45. In another embodiment, loops 35 are smaller in size than loops 45. Size of loops 35 and 45 is determined by the lengths of slits 31 and 41 respectively. Therefore, absolute and relative lengths of slits 31 and 41 can be varied to achieve desired absolute and relative sizes of loops 35 and 45.

In at least some embodiments, loops 45 of the proximal side 40 are radially offset from loops 35 of the distal side 30 to provide a better distribution of forces around the aperture 18. This can be achieved by making cuts to create slits 31 and 41 such that they are radially offset relative to each other. The maximum degree of offset will depend on the number of slits. In general, if slits are equally spaced, the maximum possible offset will be one half of the angle between the loops. For example, if distal side 30 (or proximal side 40) contains 4 slits (and therefore 4 loops), loops will be 90 degrees apart (see the formula described above), thereby allowing for maximum degree of offset of one half of 90 degrees (which is 45 degrees) between loops 35 and loops 45. In a preferred form, when distal side 30 (or proximal side 40) contains 4 slits (and therefore 4 loops), loops 45 and loops 35 are offset by 45 degrees. In an alternative embodiment, the degree of offset between loops 35 and 45 ranges from about 30 to about 45 degrees. In other embodiments, rather than forming loops 35 and 45, either one or both of the distal or proximal struts 32 and 42 can be formed to bend at the outermost point, forming a V shape. In various embodiments, many other variations on loops 35 and 45 are possible. For example, loops 35 and 45 can be formed by angled cuts, individual loops can be formed by slits of different shapes, including slits that are not straight, individual loops can have varying dimensions, and slits can be formed to provide thick and thin segments or to predispose bending at certain points. In other embodiments, the loops 35 and 45 could be radially offset. Considerations that may be important for the design of loops 35 and 45 include providing sufficient compressive force to the septal tissue to close the aperture, sufficient stiffness to withstand deployment stresses, improved collapsibility and/or transformability, improved conformance with anatomical landmarks, or the anatomy of an individual patient's heart. In some embodiments, the loops 35 and 45 could be formed according to a different cutting pattern, wherein to form either of loops 35 or 45, one portion of the tube is cut in half to form half sections and the half sections are further cut from a middle portion to a proximal distance from the end to split them into quarter sections along a length. The cuts are discontinued and one pair of quarter sections form one half section at the end, and one pair of quarter sections form another half section at the end. Adjacent loops share a common strut along a portion (i.e., provided by the half sections.) This embodiment of the loops is further described and illustrated in U.S. application Ser. No. 10/890,784, incorporated by reference herein, particularly FIGS. 2A through 2D.

The center slits 51 define struts 52 that arc outward in the deployed configuration. The struts 52 form curved ribs 57 that provide an expandable center portion 56. In some embodiments, the distal joint 55 and the proximal joint 53 are disposed on either side of the expandable center portion 56. Given that the distal and proximal joints 55 and 53 are not cut and do not include openings, they maintain the tubular profile upon the transformation of the occluder 20 to the deployed configuration. The expandable center portion 56 is thus distinct and separated from the distal and proximal loops 35 and 45. The expandable center portion 56 is adapted to be seated within the aperture 18, being closed by the occluder 20. The expandable center portion 56 provides a flexible, secure fit within the aperture 18 and prevents the occluder 20 from sliding to one side or the other once it has been deployed. The expanded center portion 56 controls the position of the occluder 20 within or over a defect. The expandable center portion 56 can accommodate the anatomical variability of cardiac defects, without requiring an occlusion device that has an overall larger size. Occluder 20, therefore, can be used in patients with varying size cardiac defects, without interfering with other anatomical features of the heart and without incurring unduly high stress levels once deployed. In the deployed configuration, the center portion 56 may be subject to radially inward compressive force or may be fully expanded, depending on the size of the aperture 18 in the individual patient. In some embodiments, the struts 52 could also form other configurations than curved ribs 57 in the deployed configuration, such as curved loops or flat loops or flat or bent ribs, thereby providing center portions with different profiles, and diameters in particular, and different radial forces.

Although the center portion 25 is illustrated as being axially aligned with the distal portion 30 and the proximal portion 40, in some embodiments, the center portion 25 could be angled relative to one side or both sides. An occluder having a straight center portion 25 is particularly suited to treat an anatomical anomaly including a perpendicular aperture, such as an ASD or certain PFOB. Often however, anatomical anomalies such as certain PFOB, have non-perpendicular apertures and are sometimes quite significantly non-perpendicular. An angled center portion 25 is well-suited to treat such defects because the angle is more likely to match the orientation of the defect. The angle can be from about 0 to about 45 degrees in some embodiments. Also, the length of the central portion 25 and the relative length of slits 51 can be varied depending on the anatomy of the defect being closed.

The tube(s) 22 forming occluder 20 includes a biocompatible metal or polymer. In at least some embodiments, the occluder 20 is formed of a bioabsorbable polymer, or a shape memory polymer. In other embodiments, the occluder 20 is formed of a biocompatible metal, such as a shape memory alloy (e.g., nitinol). The thermal shape memory and/or superelastic properties of shape memory polymers and alloys permit the occluder 20 to resume and maintain its intended shape in vivo despite being distorted during the delivery process. In addition, shape memory polymers and metals can be advantageous so that the structure of the device assists in compressing the PFO tunnel closed. Alternatively, or additionally, the occluder 20 may be formed of a bioabsorbable metal, such as iron, magnesium, or combinations of these and similar materials. Exemplary bioabsorbable polymers include polyhydroxyalkanoate compositions, for example poly-4-hydroxybutyrate (P4HB) compositions, disclosed in U.S. Pat. No. 6,610,764, entitled Polyhydroxyalkanoate Compositions Having Controlled Degradation Rate and U.S. Pat. No. 6,548,569, entitled Medical Devices and Applications of Polyhydroxyalkanoate Polymers, both of which are incorporated herein by reference in their entirety.

The cross-sectional shape of tube 22 may be circular or polygonal, for example square, or hexagonal. The slits 31 and 41 and 51 may be disposed on the face of the polygon (i.e., the flat part) or on the intersection of the faces.

The tube 22 can be extruded or constructed of a sheet of material and rolled into a tube. The sheet of material could be a single ply sheet or multiple ply. The slits that form the struts could be cut or stamped into the tube prior to rolling the tube to connect the ends to form an enclosed cross section. Various geometrical cross sections are possible including circular, square, hexagonal and octagonal and the joint could be at the vertex or along the flat of a wall if the cross section is of a particular geometry. Various attachment techniques could be used to join the ends of the sheet to form a tube, including welding, heat adhesives, non-heat adhesives and other joining techniques suitable for in-vivo application.

In alternate embodiments, the occluder 20 can be formed by aligning and selectively bonding a plurality of filaments to provide a similar geometry. In such filament-based embodiments, occluder 20 is preferably formed without cutting. References to a tube 22 as used herein are generally intended to include a tube-formed body or a filament-formed tubular body. One of skill in the art will appreciate that in lieu of "cutting" slits, slits are formed in some embodiments by selective bonding to leave openings. One of skill in the art will appreciate that occluder 20 if formed by bonding filaments, rather than by cutting a tube, will have different structural properties and will behave differently under physical stresses than an occluder formed by cutting. Techniques for forming occluders by bonding rather than by cutting are described in U.S. application Ser. No. 11/728,694, entitled Patent Foramen Ovale (PFO) Closure Device with Linearly Elongating Petals, filed Mar. 27, 2007, incorporated herein by reference.

The surface of tube 22 may be textured or smooth. An occluder 20 having a rough surface produces an inflammatory response upon contact with septal tissue 12 in vivo, thereby promoting faster tissue ingrowth, healing, and closure of aperture 18a (shown in FIG. 1). Such a rough surface may be produced, for example, by shaving tube 22 to produce whiskers along its surface. For example, the tube 22 may include such whiskers. Additionally or alternatively, the surface of tube 22 may be porous to facilitate cell ingrowth.

The tube 22 can also be preformed or partially preformed to have its deployed configuration, in order to shape the curves and bends of the respective loops and ribs. In some embodiments, the loops 35 and 45 are preformed, but the ribs 57 are not preformed. This can be desirable because the loops 35 and 45 bend more sharply than the ribs 57, and the sharp bending can be facilitated by preforming.

According to some embodiments of the invention, occluder 20 is fixed in the deployed configuration with a cooperating catch system, preferably comprising a catch member. In certain embodiments, a catch member designed for use with the occluder 20 has tubular catch body, a distal flange for engaging the distal end 62 of the tube and a proximal catch mechanism for engaging the proximal end 60 of the tube. The catch member is disposed in a central axial passage in the tube 22 and is shorter than the elongated axial length of the tube 22. For deployment, one end of the tube 22, typically the proximal end is able to slide distally, when the appropriate forces are applied, over the catch member, shortening the axial length of the tube 22. When the proximal catch mechanism is engaged, the occluder tube 20 is fixed in the deployed configuration. The proximal catch mechanism could be a deformable flap, a threaded catch mechanism, a collapsible ridge or other mechanism for holding the proximal end 60 of the occluder 20 fixed relative to the distal end 62 and preventing it from moving proximally. Some embodiments of catch members that are suitable for use with the presently disclosed embodiments are discussed in applications referenced below, which are incorporated herein by reference. One skilled in the art will recognize that the catch system may assume numerous configurations while retaining its capability to reduce and maintain the axial length of occluder 20 so that occluder 20 maintains it deployed state. One exemplary embodiment of a catch member and its deployment is schematically illustrated in FIGS. 9-12, discussed further below.

FIGS. 9-12 illustrate a deployment sequence for occluder 20 according to an embodiment of the invention. A delivery assembly 200 for delivering and deploying the occluder 20 to the desired site, i.e., aperture 18, is shown. Delivery assembly includes a delivery sheath 210, the lumen of which contains at its distal end occluder 20 in its low-profile, elongated delivery configuration and catch member 100 disposed within the axial passage of the occluder 20. The delivery sheath 210 further contains a delivery catheter 220 slidably disposed within the delivery sheath 210 and a delivery wire 230 slidably disposed within a lumen of delivery catheter 220. The delivery catheter 220 connects to the proximal end 60 of the occluder 20. In the illustrated embodiment, the connection is a threaded connection to threaded portion 70 of proximal end 60. The delivery wire 230 connects to a proximal end of the catch member 100. The components of delivery assembly 200 are dependent on, among other factors, the catch mechanism that is used. The delivery assembly should enable application of the appropriate forces to shorten the axial length of the occluder and engage the catch system. In the illustrated embodiment, the catch member 100 provides a deformable flap catch mechanism. The catch member 100 has a distal flange 110, an elongated catch body 120, and a proximal deformable flap 130. The delivery wire can connect to the proximal end of the catch member 100 by a threaded catch mechanism, for example. Delivery assemblies suitable for use with the occluder 20 are discussed in applications referenced below, which are incorporated herein by reference, and particularly U.S. application Ser. No. 11/235,661, entitled Occluder Device Double Securement System For Delivery/Recovery Of Such Occluder Device, filed Sep. 25, 2005. However, it is understood that other delivery systems may be used with the embodiments disclosed here, and, thus, the invention is not limited to any particular delivery system.

As delivery assembly 200, as shown in FIG. 9, is used to deliver the components to the desired implantation site. In its elongated, low-profile configuration, the occluder 20 is readily deliverable through a catheter system as shown. The delivery assembly 200 is introduced to a distal side of the aperture 18 (not shown). FIG. 10 illustrates a step in the deployment process. The delivery sheath 210 is retracted (or the internal components advanced) to expose the distal side 30 of the occluder 20 and the catch member 100. The proximal end of the catch member 100 is advanced in the proximal direction relative to the distal portion 30 of the occluder 20, until the flap 130 engages the distal joint 55. This step shortens the axial length of the distal portion 40, causing the bending of struts 32 and the expansion of the profile of the distal portion 30 of the occluder 20.

As shown in FIG. 11, the expanding center portion 56 is then deployed in the aperture (not shown) using a similar series of steps. The delivery sheath 210 is withdrawn to expose the center portion 25. The proximal end of the catch member 100 is advanced in the proximal direction relative to the center portion 25 until the flap engages the proximal joint 53. This step shortens the axial length of the center portion 25 (and further shortens the axial length of distal portion 30), causing the bending of struts 52 and the expansion of the profile of the center portion 25. The distal loops 35 continue to form.

As shown in FIG. 12, the proximal portion 40 is then deployed on the proximal side of the aperture (not shown) using a similar series of steps. The delivery sheath 210 is further retracted to expose the proximal portion 40. The proximal end of the catch member 100 is advanced in the proximal direction relative to the center portion 25 until the flap 130 engages the proximal end 60. This step shortens the axial length of the occluder 20, causing the bending of struts 42 and the expansion of the profile of the proximal portion 40. This step completes the transformation to the deployed configuration of occluder 20. Loops 35 and 45 and ribs 57 are fully formed upon completion of this step. The deployment is completed by releasing and withdrawing the delivery assembly 200. The fully deployed occluder 20 is illustrated in FIG. 2. When fully deployed, occluder 20 rests within the aperture 18, and the distal side 30 and proximal side 40 exert a compressive force against septum primum and septum secundum in the left and right atria, respectively to close the aperture 18. If the deployment is not satisfactory, the occluder 20 can be retrieved and redeployed. The techniques disclosed for deploying the embodiments described herein are only one example of a deployment technique, it being understood that other techniques can be used instead of, or in combination with, those disclosure. For example, the techniques used to deploy an embodiment of the occluders described herein will depend on the particular features of the occluder, the delivery system, and the anatomy in which the occluder is being deployed.

Figure 13:
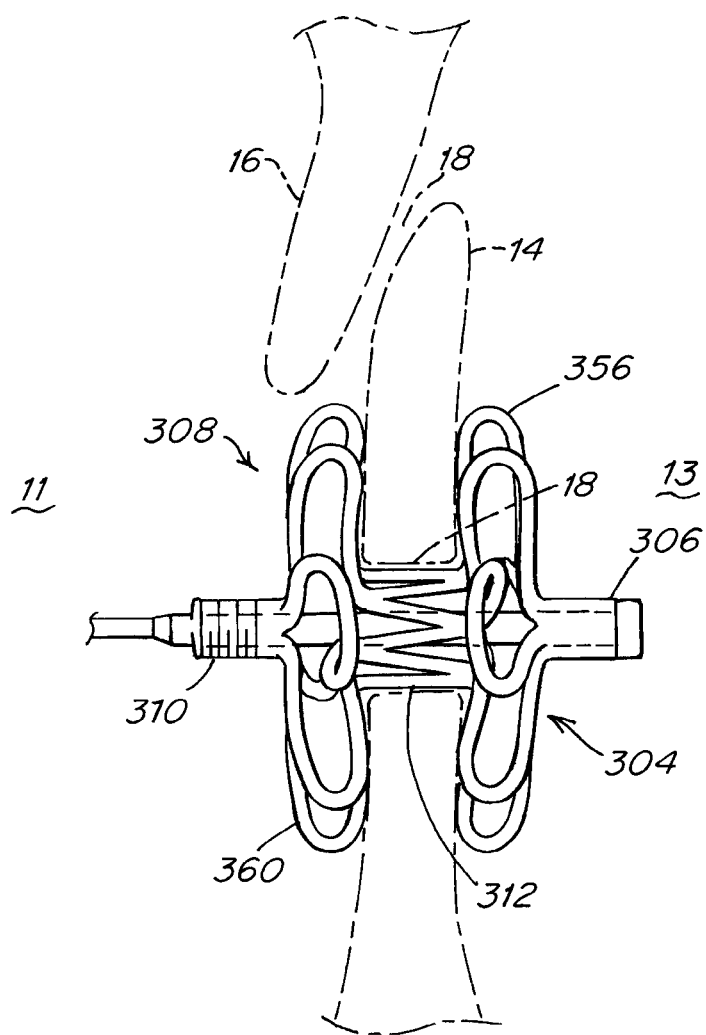
FIG. 13 is view of an occluder deployed in the heart of a patient according to an embodiment of the invention.

FIG. 13 illustrates an embodiment of the occluder 300 according to a further aspect of the invention. Similar to the embodiment of FIG. 2, the occluder 300 has a distal side 304 and a distal end 306, along with a proximal side 308 and a proximal end 310, disposed on respective sides of an aperture 18. The distal side 304 and the proximal side 308 include features that cooperate to provide a compressive force against the septum primum and the septum secundum when in the deployed position. The distal side 304 and proximal side 308 are connected by a central portion 312, which is discussed below in more detail. The occluder 300 may be inserted into the septal tissue, e.g., septum secundum and/or septum primum, such that the distal side 304 is located in the left atrium 13, the proximal side 308 is located in the right atrium 11, and the expandable central portion 312 provides a self centering mechanism.

In FIG. 13, the aperture 18 in the septum primum 14 may be an ASD. Thus, occluder 300 may be deployed within aperture 18 to occlude this type of defect. Although not shown in the figure, an ASD may also exist in the septum secundum 16. Occluder 300 may also be deployed in an ASD in this portion of the septal tissue. Aperture 18 in the septum primum 14 can also be a man-made aperture created for the purpose of occluding a PFO-type of defect. In such a case, the proximal loops 360 of the occluder 300 are sized so as to overlap a portion of the septum secundum 16 and pinch the PFO closed. The distal loops 356 are sized to compliment the size of the proximal loops 360. In this configuration, the occluder 300 applies a compression force to the septum primum 14 and septum secundum 16 without being disposed in the PFO tunnel 18. However, it is understood that the occluder 300 can also be deployed within the PFO tunnel 18, as described herein.

Referring now also to FIGS. 14-18, providing perspective views of the occluder 300, in the illustrated embodiment, the occluder 300 maybe constructed of one or more metal or polymer tube(s) or filaments, forming a body referred to collectively as tube 316. Tube 316 includes slits 364, 368, 372, and 376, etc., which in some embodiments may be formed using an etching or cutting process that produces a particular cutting pattern on tube 316. Similar to previous embodiments, it will be appreciated that the slits may extend around the entire circumference of the tube in accordance with the patterning represented in FIG. 14.

Figure 14:
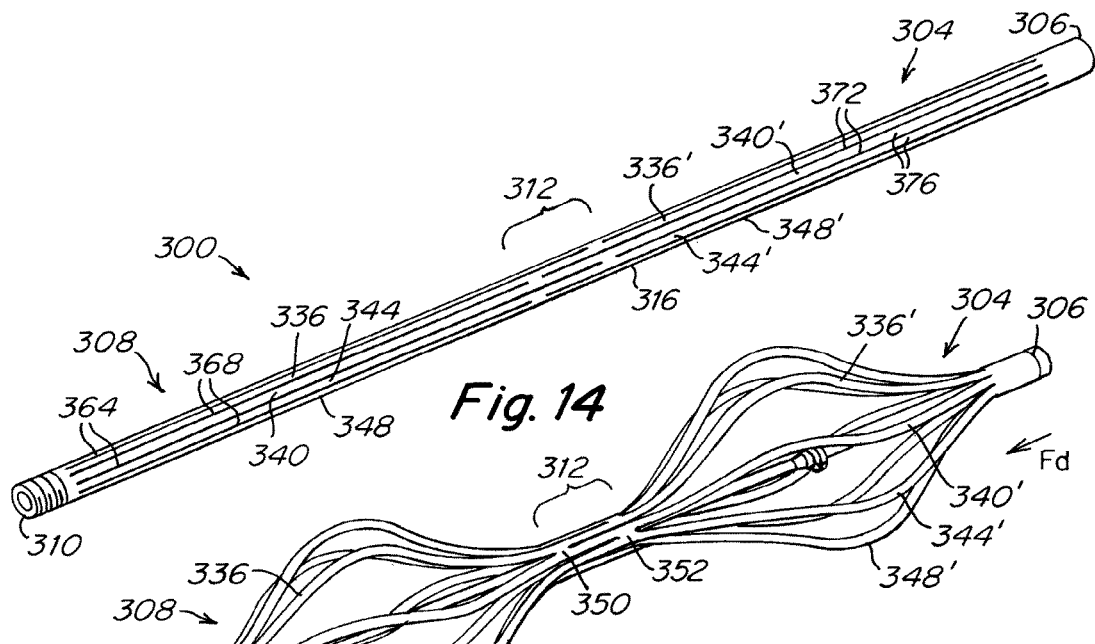
FIGS. 14-17 are isometric views of an embodiment of an occluder according to an exemplary embodiment of the present invention.
Figure 15:
Figure 16:
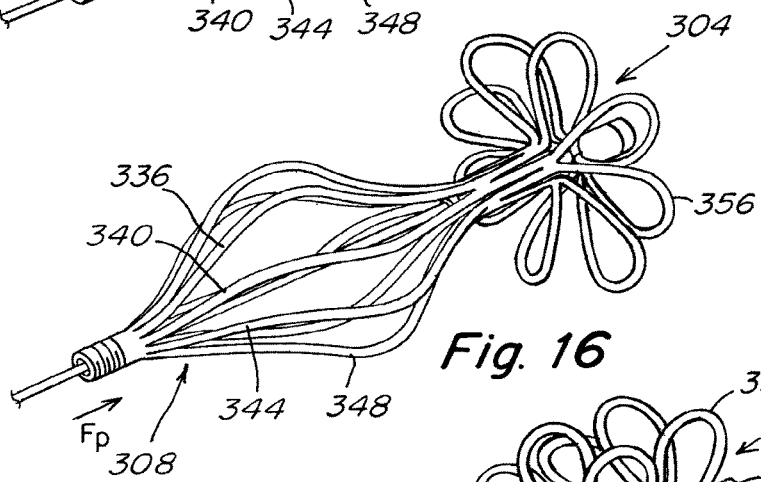

The formation of the slits 364, 368, 372, and 376 provide struts around the tubes' 316 circumference. For example, as shown in FIG. 14, struts 336, 340, 344 and 348 extend from the proximal side 308 of the tube 316, and the struts 336', 340', 344' and 348' extend from the distal side 304 of the tube 316, so as to be joined with adjacent struts at convergence areas or joints 350 and 352 (shown in FIG. 15). For example, the convergence area 350 is provided where the struts 336 and 340 are joined, and convergence area 352 is provided where struts 340' and 344' are joined. The joints 350 and 352 maybe repeated around the circumference to the tube 316 to form a zigzag pattern at the expanded central portion 312 as illustrated in the exemplary embodiment of FIG. 18. Due to the nature of the slits, the corresponding struts, e.g., 336 and 336', may in some embodiments be considered to form one continuous strut, as show in the figures.

The occluder 300 is transformable from a delivery configuration to a deployed configuration. FIG. 14 approximates the delivery configuration of the occluder 300. The transformation is represented in FIGS. 14-17, and the fully deployed condition, in a human heart, is illustrated in FIG. 13. Similar to the previous embodiment, the occluder 300 can be delivered via a catheter assembly, such as catheter system 124, shown in FIG. 3, and has a tubular delivery configuration well-suited for delivery via the catheter system 124. The deployed configuration is attained by shortening the axial length of the tube 316 and catching the occluder 300 in that configuration. Portions of the struts 336, 340, 344 and 348 at the proximal side 308 form loops 360, and portions of the struts 336', 340', 344' and 348' at the distal side 304 form loops 356 when the occluder 300 is in the deployed configuration. As a compression force is applied and the loops 356 and 360 extend in the radial direction, an outward force is exerted onto the center portion 312 to assist the center portion 312 in radially expanding, as shown by the size progression of the central portion 312 in FIGS. 14-17. Accordingly, the central portion 312 is subject to a uniform distribution of forces causing the respective portions of the struts and joints in the central portion 312 to be displaced outwardly by a uniform amount, providing the central portion with a cylindrical-like appearance with ends that eventually curve outwardly near the convergence areas 350 and 352.

Figure 17:
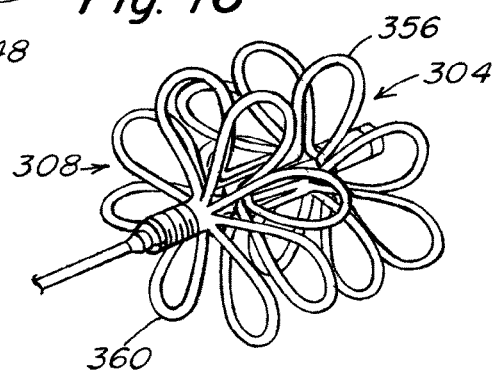
Figure 18:
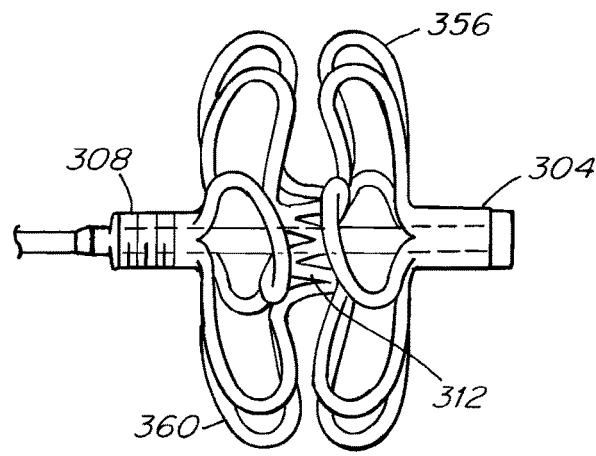
FIG. 18 is a schematic representation of an occluder according to an embodiment of the invention in a compressed state.

The shape of the occluder 300 in the deployed configuration is determined by the cutting pattern on tube 316. For example, and as shown in FIGS. 13, 17 and 18, the petal-shaped loops 356 and 360 are produced by cutting slits 364 and 368 in the proximal side 308 of tube 316, and cutting slits 372 and 376 in the distal side 304 of tube 316 according to the cutting pattern shown in FIG. 14. The slits 364, 368, 372 and 376 may be longitudinally and equally spaced apart around the circumference of the tube 316. The slits 364 and 368 alternative in length such that the slits 364 extend further in the axial direction toward the center portion 312 than slits 368. Similarly, the slits 372 and 376 alternative in length such that the slits 376 extend further in an opposite axial direction toward the center portion 312 than the slits 372. It will be appreciated that the pattern formed by the slits 364, 368, 372 and 376 may be repeated around the circumference of the tube occluder 300. Slits 364 may extend to overlap with at least a portion of slits 376. The lengths and positioning of slits 364, 368, 372 and 376 contribute to the central portion 312 exhibiting substantially uniform expansion in the area between the convergence points 350 and 352, to provide a more balanced distribution of forces along the center portion 312 and help prevent the center portion 312 from be biased to any one side of the septum primum, as shown in FIG. 13. By altering the length of the slits, the convergence areas 350 and 352 are located at different points along the axial direction, and can be patterned to provide the expanded central portion 312 with the zigzag pattern, show in the exemplary embodiment of FIG. 18.

Upon application of force $F_d$ to end 306 to shorten the axial length of distal side 304, struts 336', 340', 344' and 348' bow and twist outward to form the petal-shaped loops 356 in distal side 304. The movement of the struts 336', 340', 344' and 348' during deployment is such that the struts rotate in an orthogonal plane relative to the axis of the device. The petal-shaped loops 356 bend outwardly from center portion 312 and terminate towards the end 306. The struts 336, 340, 344 and 348 of the proximal side 308 act in a similar manner when a force $F_p$ is applied.

The expandable center portion 312 extends into the distal and proximal loops 356 and 360. The expandable center portion 312 is adapted to be seated within the aperture 18, being closed by the occluder 360. The expandable center portion 312 provides a flexible, secure fit and helps prevent the occluder 360 from sliding to one side or the other once it has been deployed.

Certain embodiments of the present invention have certain similarities to devices and/or may be used with a number of delivery and catch systems such as those described in U.S. application Ser. No. 10/731,547, entitled Septal Closure Devices, filed Dec. 9, 2003; U.S. application Ser. No. 11/121,833, entitled Catching Mechanisms for Tubular Septal Occluder, filed May 4, 2005; U.S. application Ser. No. 11/235,661, entitled Occluder Device Double Securement System for Delivery/Recovery of such Occluder Device, filed Sep. 26, 2005; U.S. application Ser. No. 11/384,635, entitled Catch Member for PFO Occluder, filed Mar. 20, 2006; U.S. application Ser. No. 11/644,373, entitled Catch Members for Occluder Devices, filed Dec. 21, 2006;

U.S. application Ser. No. 11/111,685, entitled Closure Device with Hinges, filed Apr. 21, 2005; U.S. application Ser. No. 11/729,045, entitled Screw Catch Mechanism for Occluder and Method of Use, filed Mar. 28, 2007; U.S. application Ser. No. 11/729,637, entitled Deformable Flap Catch Mechanism for Occluder Device, filed Mar. 29, 2007; U.S. application Ser. No. 11/728,694, entitled Patent Foramen Ovale (PFO) Closure Device with Linearly Elongating Petals, filed Mar. 27, 2007; U.S. application Ser. No. 11/904,545, entitled Implant Catheter Attachment Mechanism Using Snare and Method of Use, filed Sep. 27, 2007, and U.S. application Ser. No. 11/395,718, entitled Tubular Patent Foramen Ovale (PFO) Closure Device With Catch System, filed Mar. 31, 2006, all of which have the same assignee as the present application and are herein incorporated by reference.

In some embodiments, the device includes a tissue scaffold. In various embodiments, the tissue scaffold can be formed of any flexible, biocompatible material capable of promoting host tissue growth including, but not limited to, polyester fabrics, Teflon-based materials, such as ePTFE, polyurethanes, metallic materials, polyvinyl alcohol (PVA), extracellular matrix (ECM) isolated from a mammalian tissue, or other bioengineered materials, bioabsorbable polymers, or other natural materials (e.g., collagen), or combinations of these materials. Furthermore, the surface of the tissue scaffold can be modified with biological, pharmaceutical and/or other active ingredients, such as anti-coagulants, anti-thrombogenic agents, cells, growth factors and/or drugs to improve defect healing and/or to prevent blood clotting. The scaffold can be attached to a cardiovascular occluder frame or to another scaffold by sutures, heat treatment, adhesives, or any other chemical bonding process.

Figure 19:
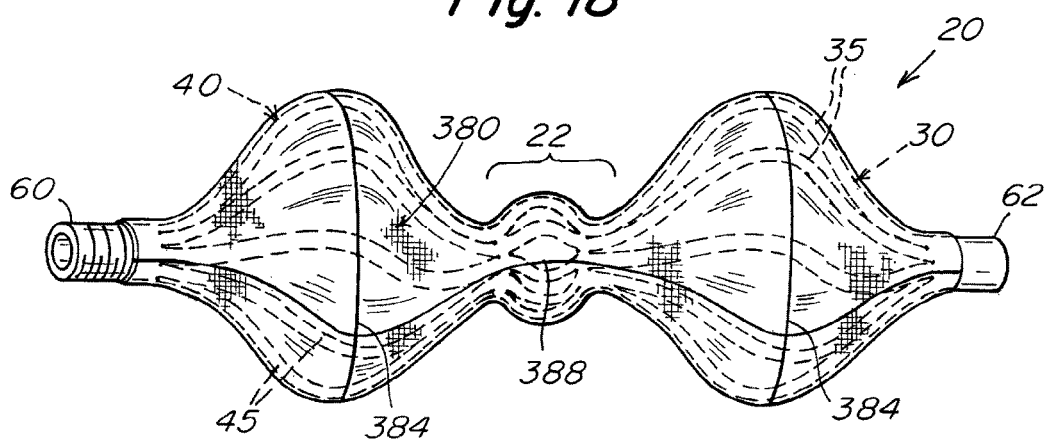
FIG. 19 is a perspective view of an embodiment of an occluder with a tissue scaffold.
Figure 20:
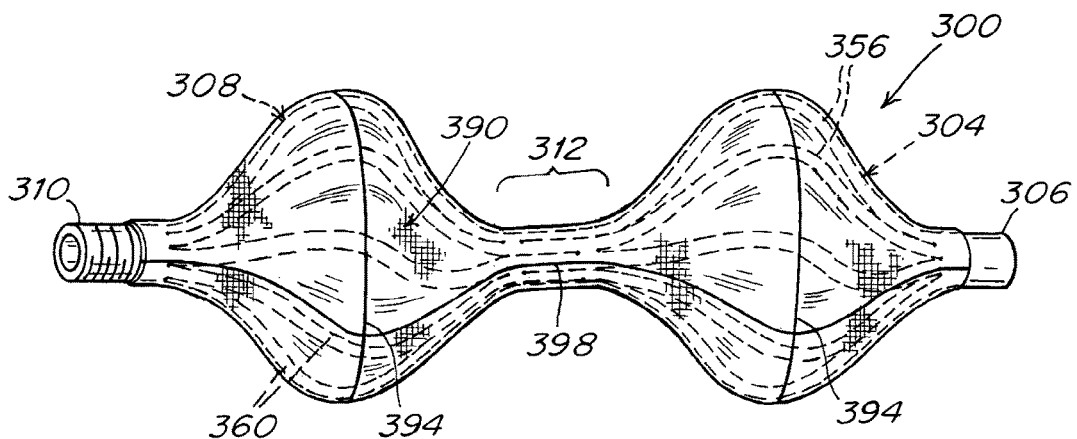
FIG. 20 is a perspective view of an embodiment of an occluder with a tissue scaffold according to the present invention.

A tissue scaffold is described and illustrated with respect to the occluders 20 and 360 in FIGS. 19 and 20; however, a tissue scaffold used with the present exemplary embodiments may be in the form of any suitable embodiments described in U.S. application Ser. No. 11/904,137, entitled Scaffold For Tubular Septal Occluder Device And Techniques For Attachment, filed Sep. 26, 2007, which application has the same assignee as the present application and is incorporated herein in its entirety by reference.

As shown in FIG. 19, a scaffolded occluder 20 includes the occluder 20 and a tissue scaffold 380. In this embodiment, the tissue scaffold 380 completely encapsulates the occluder petals 35 and 45, and the central portion 25. The coverage provided by tissue scaffold 380 offers several aspects, including that the tissue scaffold 380 improves the sealing of the aperture being closed. Another advantage is that the tissue scaffold can enhance the implant's stability at the desired delivery location. The tissue scaffold can allow and facilitate the ingrowth of tissue, and certain pharmacological agents can be applied or embedded in the tissue scaffold for delivery to the implant site. The tissue scaffold 380 includes seams, such as seams 384 and 388. The presence of such seams may impact the dimensions of the occluder, the size of delivery catheter to be used and other aspects of the use of the occluder.

As shown in FIG. 20, a scaffolded occluder 300 includes the occluder 300 and a tissue scaffold 390. Similar to the above embodiment, in the embodiment of FIG. 15B the tissue scaffold 390 completely encapsulates the occluder petals 356 and 360, and the central portion 312. The tissue scaffold likewise 390 includes seams, such as seams 394 and 398.

One skilled in the art will recognize that the occluders described herein may be used with various drugs, growth factors, and/or other agents to improve defect healing and/or to prevent blood clotting. Such agents include but not limited to Adenovirus with or without genetic material; Angiogenic agents; Angiotensin Converting Enzyme Inhibitors (ACE inhibitors); Angiotensin II antagonists; Anti-angiogenic agents; Antiarrhythmics; Anti-bacterial agents; Antibiotics: Erythromycin, Penicillin; Anti-coagulants: Heparin; Anti-growth factors; Anti-inflammatory agents: Dexamethasone, Aspirin, Hydrocortisone; Antioxidants; Anti-platelet agents; Forskolin; Anti-proliferation agents; Anti-rejection agents; Rapamycin; Anti-restenosis agents; Antisense; Anti-thrombogenic agents; Argatroban Hirudin; GP IIb/IIIa inhibitors; Antivirus drugs; Arteriogenesis agents; acidic fibroblast growth factor (aFGF); angiogenin; angiotropin; basic fibroblast growth factor (bFGF); Bone morphogenic proteins (BMP); epidermal growth factor (EGF); fibrin; granulocyte-macrophage colony stimulating factor (GM-CSF); hepatocyte growth factor (HGF); HIF-1; insulin growth factor-1 (IGF-1); interleukin-8 (IL-8); MAC-I; nicotinamide platelet-derived endothelial cell growth factor (PD-ECGF); platelet-derived growth factor (PDGF); transforming growth factors alpha & beta (TGF-a, TGF-b); tumor necrosis factor alpha (TNF-a); vascular endothelial growth factor (VEGF); vascular permeability factor (VPF); Bacteria Beta blocker; Blood clotting factor; Calcium channel blockers; Carcinogens; Cells; Bone marrow cells; Blood cells; Stem Cells; Umbilical cord cells; Fat cells; Chemotherapeutic agents (e.g. Ceramide, Taxol, Cisplatin); Cholesterol reducers; Chondroitin Collagen Inhibitors; Colony stimulating factors; Coumadin; Cytokines; prostaglandins; Dentin Etretinate Genetic material; Glucosamine; Glycosaminoglycans; L-703, 081; Growth factor antagonists or inhibitors; Growth factors; Autologous Growth Factors; Basic fibroblast growth factor (bFGF); Bovine Derived Growth Factors; Cartilage Derived Growth Factors (CDF); Endothelial Cell Growth Factor (ECGF); Fibroblast Growth Factors (FGF); Nerve growth factor (NGF); Recombinant NGF (rhNGF); Recombinant Growth Factors; Tissue Derived Cytokines; Tissue necrosis factor (TNF); Growth hormones; Heparin sulfate proteoglycan; HMC-CoA reductase inhibitors (statins); Hormones; Erythropoietin; Immoxidal; Immunosuppressant agents; inflammatory mediator; Insulin; Interleukins; Lipid lowering agents; Lipo-proteins; Low-molecular weight heparin; Lymphocytes; Lysine; Morphogens Nitric oxide (NO); Nucleotides; Peptides; PR39; Proteins; Prostaglandins; Proteoglycans; Perlecan Radioactive materials; Iodine—125; Iodine—131; Iridium—192; Palladium 103; Radiopharmaceuticals; Secondary Messengers; Ceramide; Somatomedins; Statins; Steroids; Sulfonyl Thrombin; Thrombin inhibitor; Thrombolytics; Ticlid; Tyrosine kinase; Inhibitors; ST638; AG17; Vasodilator; Histamine; Nitroglycerin; Vitamins E and C; Yeast. The occluders could also be modified so as to deliver one or more alarmin(s) or alarmin activator(s), or a combination of alarmin(s) and alarmin activator(s) to the intracardiac tissue to be treated to accelerate recruitment of endogenous cells, for example, fibroblasts, myocytes, endothelial cells and their progenitors, and progenitor cells of the circulating blood, formation of granulation tissue and re-endothelialization at the site of the intracardiac defect. Exemplary alarmins include members of the family of damage associated molecular pattern molecules (DAMPs) and members of the family of pathogen associated molecular pattern molecules (PAMPs). Exemplary alarmins further include the nuclear protein HMGB1, the S100 family of molecules (cytosolic calcium-binding proteins), heat shock proteins, interleukins (including IL-1a), HDGF (hepatoma-derived growth factor, Gall (Galectin 1) and the purinergic metabolites of ATP, AMP, adenosine and uric acid. Alarmin activators include small molecules necessary for maintaining the activity of administered and/or endogenous alarmins. Exemplary alarmin activators include thiol containing reducing agents, including, but not limited to, dithiothreitol, 2-mercaptoethanol, N-7-acetyl-cysteine, sodium sulfite, glutathione, and Probucol™ (2,6-ditert-butyl-4-[2-(3,5-ditert-butyl-4-hydroxyphenyl)sulfanylpropan-2-ylsulfanyl]phenol). Exemplary alarmin activators further include non-thiol reducing agents, including, but not limited to, ascorbic acid, sodium hypophosphite, and sodium borohydride."

One skilled in the art will further recognize that occluders according to the invention could be used to occlude other vascular and non-vascular openings. For example, the device could be inserted into a left atrial appendage or other tunnels or tubular openings within the body.

Various embodiments have been illustrated and described herein by way of example, and one of skill in the art will appreciate that variation can be made without departing from the spirit and scope of the invention.

What is claimed is:

1. A device for occluding a defect in a body, the device comprising:
   an occluder body that defines a longitudinal axis, the occluder body being reconfigurable from an elongated delivery configuration to a shortened and radially expanded deployed configuration, the occluder body comprising:
   a proximal end portion;
   a proximal convergence area that is positioned distal of the proximal end portion;
   a plurality of proximal-side struts that extend between the proximal end portion and the proximal convergence area to define a proximal side;
   a distal convergence area that is positioned distal of the proximal convergence area;
   a plurality of central struts that extend between the proximal convergence area and the distal convergence area to define a central portion, wherein portions of the plurality of central struts are non-overlapping and form a substantially cylindrical area while the occluder body is configured in the deployed configuration;
   a distal end portion that is positioned distal of the distal convergence area; and
   a plurality of distal-side struts that extend between the distal convergence area and the distal end portion to define a distal side,
   wherein each of the proximal end portion, the proximal convergence area, the distal convergence area, and the distal end portion are disposed generally coaxially in relation to the longitudinal axis while the occluder body is configured in the delivery configuration,
   wherein while the occluder body is configured in the delivery configuration each of: (i) the plurality of proximal-side struts, (ii) the plurality of central struts, and (iii) the plurality of distal-side struts are arranged radially outward from the longitudinal axis while each of: (a) the proximal end portion, (b) the proximal convergence area, (c) the distal convergence area, and (d) the distal end portion remain disposed generally coaxially in relation to the longitudinal axis and in the deployed configuration, a portion of each of the plurality of proximal-side struts overlap with a portion of at least one of the plurality of proximal-side struts adjacent thereto at a discrete location and a portion of each of the plurality of distal-side struts overlap with a portion of at least one of the plurality of distal-side struts adjacent thereto at a discrete location.

2. The device of claim 1, wherein in the deployed configuration the plurality of proximal-side struts form a plurality of proximal-side petal-shaped loops and the plurality of distal-side struts form a plurality of distal-side petal-shaped loops.

3. The device of claim 2, wherein an expanded radius of the central portion is less than an expanded radius of the plurality of proximal-side petal-shaped loops and is less than an expanded radius of the plurality of distal-side struts while the occluder is in the deployed configuration.

4. The device of claim 2, wherein each proximal-side petal-shaped loop of the plurality of proximal-side petal-shaped loops overlaps with one or more other proximal-side petal-shaped loops of the plurality of proximal-side petal-shaped loops.

5. The device of claim 2, wherein a total number of proximal-side petal-shaped loops of the plurality of proximal-side petal-shaped loops is unequal to a total number of distal-side petal-shaped loops of the plurality of distal-side petal-shaped loops.

6. The device of claim 2, wherein the plurality of proximal-side petal-shaped loops are radially offset from the plurality of distal-side petal-shaped loops.

7. The device of claim 1, wherein the occluder body is formed from a tube,
   wherein each of the plurality of proximal-side struts, the plurality of distal-side struts, and the plurality of central struts are defined by slits in the tube,
   and wherein each of the proximal end portion, the proximal convergence area, the distal convergence area, and the distal end portion comprise portions of the tube that do not include slits such that at least the distal convergence area and the proximal convergence area are configured to maintain a non-expanded tubular profile upon a reconfiguration of the occluder body from the delivery configuration to the deployed configuration.

8. The device of claim 1, wherein the central portion comprises a different number of struts than at least one of the distal and proximal sides of the occluder body.

9. A device for occluding a defect in a body, the device comprising:
   an occluder body that defines a longitudinal axis, the occluder body being reconfigurable from an elongated delivery configuration to a shortened and radially expanded deployed configuration, the occluder body comprising:
   a proximal end portion;
   a proximal convergence area that is positioned distal of the proximal end portion;
   a plurality of proximal-side struts that extend between the proximal end portion and the proximal convergence area to define a proximal side;
   a distal convergence area that is positioned distal of the proximal convergence area;
   a plurality of central struts that extend between the proximal convergence area and the distal convergence area to define a central portion, and portions of the plurality of central struts are non-overlapping and form a substantially circular perimeter while the occluder body is configured in the deployed configuration;

a distal end portion that is positioned distal of the distal convergence area; and a plurality of distal-side struts that extend between the distal convergence area and the distal end portion to define a distal side, wherein each of the proximal end portion, the proximal convergence area, the distal convergence area, and the distal end portion are disposed generally coaxially in relation to the longitudinal axis while the occluder body is configured in the delivery configuration, wherein while the occluder body is configured in the delivery configuration each of: (i) the plurality of proximal-side struts, (ii) the plurality of central struts, and (iii) the plurality of distal-side struts are arranged radially outward from the longitudinal axis while each of: (a) the proximal end portion, (b) the proximal convergence area, (c) the distal convergence area, and (d) the distal end portion remain disposed generally coaxially in relation to the longitudinal axis and in the deployed configuration, a portion of each of the plurality of proximal-side struts overlap with a portion of at least one of the plurality of proximal-side struts adjacent thereto at a discrete location and a portion of each of the plurality of distal-side struts overlap with a portion of at least one of the plurality of distal-side struts adjacent thereto at a discrete location, wherein the occluder body is formed from a tube, wherein slits in the tube define each of: (1) the plurality of proximal-side struts, (2) the plurality of distal-side struts, and (3) the plurality of central struts.

10. The device of claim 9, wherein in the deployed configuration the plurality of proximal-side struts form a plurality of proximal-side petal-shaped loops and the plurality of distal-side struts form a plurality of distal-side petal-shaped loops.

11. The device of claim 10, wherein an expanded radius of the central portion is less than an expanded radius of the plurality of proximal-side petal-shaped loops and is less than an expanded radius of the plurality of distal-side struts while the occluder is in the deployed configuration.

12. The device of claim 10, wherein each proximal-side petal-shaped loop of the plurality of proximal-side petal-shaped loops overlaps with one or more other proximal-side petal-shaped loops of the plurality of proximal-side petal-shaped loops.

13. The device of claim 10, wherein a total number of proximal-side petal-shaped loops of the plurality of proximal-side petal-shaped loops is unequal to a total number of distal-side petal-shaped loops of the plurality of distal-side petal-shaped loops.

14. The device of claim 10, wherein the plurality of proximal-side petal-shaped loops are radially offset from the plurality of distal-side petal-shaped loops.

15. The device of claim 9, wherein the plurality of central struts are parallel with the longitudinal axis while the occluder body is configured in the delivery configuration.

16. The device of claim 9, wherein the central portion comprises a different number of struts than at least one of the distal and proximal sides of the occluder body.

17. The device of claim 9, wherein each of (i) the proximal end portion, (ii) the proximal convergence area, (iii) the distal convergence area, and (iv) the distal end portion comprise portions of the tube that do not include slits.

* * * * *